(12) United States Patent
Lopes

(10) Patent No.: US 8,414,292 B2
(45) Date of Patent: Apr. 9, 2013

(54) SELF LIGATING BRACKET SYSTEM

(76) Inventor: Alexandre Gallo Lopes, Ribeirão Preto (BR)

( * ) Notice: Subject to any disclaimer, the term of this patent is extended or adjusted under 35 U.S.C. 154(b) by 142 days.

(21) Appl. No.: 12/848,689

(22) Filed: Aug. 2, 2010

(65) Prior Publication Data

US 2012/0028206 A1    Feb. 2, 2012

(51) Int. Cl.
*A61C 7/30* (2006.01)
*A61C 7/34* (2006.01)
*A61C 7/28* (2006.01)

(52) U.S. Cl.
USPC .............................................. 433/14; 433/13

(58) Field of Classification Search ................ 433/8–17, 433/24
See application file for complete search history.

(56) References Cited

U.S. PATENT DOCUMENTS

| 5,322,435 | A |   | 6/1994  | Pletcher |        |
|-----------|---|---|---------|----------|--------|
| 6,071,119 | A | * | 6/2000  | Christoff et al. | 433/14 |
| 7,621,743 | B2 |  | 11/2009 | Bathen et al. | |
| 2006/0228664 | A1 | * | 10/2006 | Castner et al. | 433/11 |
| 2008/0248440 | A1 | * | 10/2008 | Wool | 433/10 |
| 2009/0061376 | A1 | * | 3/2009  | Wool | 433/11 |
| 2010/0311004 | A1 | * | 12/2010 | Voudouris | 433/11 |

* cited by examiner

*Primary Examiner* — Todd Manahan
*Assistant Examiner* — Michael R Ballinger
(74) *Attorney, Agent, or Firm* — Arent Fox LLP

(57) ABSTRACT

A self ligating orthodontic bracket system includes a bracket, a slidable ligating member and at least one wedge locking ramp. The bracket includes an archwire slot defined therein, which is configured to receive an archwire therein. The ligating member slides along a slide path defined on the bracket and which extends transverse relative to the archwire slot. The wedge locking ramp is disposed on the slide path, wherein the wedge locking ramp is configured to deflect the ligating member vertically upward and away from an upper surface of the slide path, and over the wedge locking ramp when the ligating member travels along the slide path from an unlocked position to a locked position. The archwire is securely retained in the archwire slot when the ligating member is in the locked position.

32 Claims, 24 Drawing Sheets

SELF LIGATING BRACKET SYSTEM

BACKGROUND OF THE INVENTION

1. Field of the Invention

The invention relates to an orthodontic bracket system, more particularly, to a self ligating bracket that may include a shape memory sliding clip.

2. Brief Description of Related Art

Orthodontic treatment typically involves dental work intended to correct irregularities of the teeth or of the relation of the teeth to surrounding anatomy. The irregularities may involve malocclusions with varying degrees of severity. Examples of malocclusions include, spacing irregularities, such as excessive crowding or diastema, overbite irregularities, and underbite irregularities. Treatment of the listed exemplary irregularities, as well as others, typically involves installing braces or mechanical aids needed to reposition the teeth into an appropriate or correct orthodontic alignment.

Braces conventionally include orthodontic brackets designed to be attached to either the labial or lingual surface of a tooth. The brackets generally include archwire slots within which a flexible, yet resilient, archwire is positioned. Each bracket is affixed to the appropriate tooth surface so that the archwire slot is oriented to facilitate the archwire being positioned therein. The brackets can be oriented in a variety of ways wherein the archwire extends orthogonally or parallel relative to the long axis of the root of the tooth.

Since Dr. Edward Hartley Angle patented the Edgewise bracket in the 1920's, the biomechanical function of orthodontic brackets remains essentially unchanged. Despite significant improvements in design, state of the art manufacturing processes, and the development of new materials since the Edgewise bracket was patented, the concept of moving and having control of teeth in three dimensions remains the same. The quality and development of new materials associated with low force biological concepts has provided orthodontists with a new approach to preserving periodontal ligament integrity during the treatment of malocclusions.

The geometric configuration of the bracket incorporates an archwire slot oriented horizontally, transverse relative to the face of the bracket, with a pair of parallel walls arranged substantially perpendicular to the slot floor, which define a rectangular slot configuration in the cross section. The parallel walls are conventionally referred to as tie wings or extensions which project upwardly and away from the tooth surface.

An archwire is positioned within the archwire slot and may have varied dimensions and cross sections (e.g., round, rectangular, etc.) from which an orthodontic professional may select based on the intended use and/or need of the patient. Moreover, the configuration of the archwire may be selected based on the phase of treatment and the extent the teeth need to move during the treatment plan established by the orthodontist. For example, the archwire is known to be manufactured from metal, a metallic material, and/or a shape memory material and which can be bent or twisted prior to being inserted within the archwire slot. The memory or restorative force exerted by the archwire onto the brackets helps move the teeth to the desired alignment.

Orthodontic brackets have different features, determined statistically for values like torque, angulation, in and out, offsets, extrusions inherent to the positioning of the arch slot on a tooth by tooth basis, all of which give the orthodontist the option to individualize the set of brackets to be used in the treatment according to the facial pattern and the ideal positioning of the tooth for angulation and inclination, thereby minimizing the need for bends and adjustments on the archwires. In orthodontics, this treatment methodology is conventionally known as "Straight Wire Appliance," conception of which took place in the 1970s and is commonly attributed to Dr. Lawrence Andrews.

In the 1930s, self ligating brackets became commercially available. The primary characteristic of such brackets in the 1930s was the ease with which an archwire could be changed, which saved orthodontists significant hours of chair time. In the 1970's, numerous studies and research of friction in the archwire slot spawned a new generation of self ligating brackets which were based on the concept of low friction and sliding mechanics. Consequently, an approach was developed wherein low friction mechanics and forces were used to move teeth with ligatureless orthodontic brackets.

The use of steel ligatures or elastomeric ligatures associated with conventional brackets presents new difficulties and concerns. For example, the placement of steel ligatures is a time consuming operation that can lead to motion repetitive injuries to the orthodontic professional. Moreover, there are considerable costs associated with the specific procedures required when using the set of sterilized instruments that are dedicated to the placement of the bracket on the tooth. Also, elastomeric ties, although easier to place around the bracket than the previously used ties, deteriorate fairly rapidly within the mouth of the patient, absorb water, and accumulate excess plaque, thereby leading to an undesirable condition of the periodontum, such as inflammation. Both ligating methods, i.e., the methods which use steel ligatures and elastomeric ties, suffer from the concern of high friction forces being applied to the binary bracket/archwire once normal forces are applied, which press the archwires against the bottom of the slot and prevent the working energy that is carried by the archwire from being applied to the tooth movement. The restrictive force, independent of the treatment methodology or technique used, results in an increase in the frequency in which the archwire must be changed, as well as higher force levels being applied from the archwire to the bracket.

In the 80's, the above-mentioned low friction/low force concept gained momentum with the development of new alloys that were used in the manufacture of the archwires. The alloys were developed to have a low force modulus tailored to the force needs of the self ligating brackets. The reduced friction permitted the teeth to slide more easily during certain stages of the treatment with the low force modulus contributing to faster treatments that required less visits to the orthodontist and less pain experienced by the patient.

A difficult task in choosing the archwire that is used to move teeth is the predictability of the effective force that will be delivered by the archwire to the teeth. Restrictive forces from steel ligatures or elastomeric O-rings are variables that lead to indeterminate effective forces being used in tooth movement. Also, sometimes, the steel and elastomeric ligatures bend the archwires beyond their elastic properties, resulting in notching of the wire or plastically deforming the wire in a manner that results in a permanent bend.

Research of the self ligating bracket using state of the art force testing equipment determined that 6% to 10% of the applied force is lost due to friction. Therefore, 90% of the applied force becomes effective force used to move teeth.

Although reduced friction is desirable, there are occasions when more friction is desired, such as towards the end of the treatment plan when consolidation of the arch form in three planes is needed to stabilize the achieved result and the dental arch form. Clinical modifications or placement of more conventional brackets becomes a requirement as treatment proceeds, resulting in an increase in material cost and time consuming procedures in the office.

Further, self ligating brackets include moving parts that become distorted, warped or disengaged, thereby compromising the pace of treatment.

To date, several self-locking or self-ligating (ligatureless) orthodontic brackets have been designed. However, most brackets have complex designs, and/or incorporate features that require prohibitively expensive machining operations or include a plurality of separate parts, which in turn increases the number of failure modes for such brackets. The complexity in design and manufacturing processes for orthodontic self ligating brackets has driven prices exceedingly above the costs of a conventional bracket and without providing the option of converting the bracket when needed or replacing the clip in the event of breakage or malfunctioning.

Thus, there is a need for a self ligating orthodontic bracket to overcome the deficiencies and drawbacks of conventional self ligating brackets available today.

SUMMARY OF THE INVENTION

The inventive self ligating orthodontic bracket includes a bracket or housing having a pair of upper tie wings separated from a pair of lower tie wings by an archwire slot defined therebetween. It should be noted that any of the below described embodiments of the inventive self ligating orthodontic bracket may have a base or lower surface of the bracket which is configured to have a compound radius to better adapt to the surface of the tooth. A clip slides along a slide path defined by the upper and lower tie wings in a direction that extends from the lower tie wings to the upper tie wings and is transverse relative to the direction in which the archwire slot extends. The clip covers an opening of the slot such that an orthodontic archwire is retained in the slot. The clip is preferably manufactured from a shape memory material and includes a pair of arms, each arm preferably having a tab extending from a free end of the arm in a direction that is generally parallel to the slot and transverse to the direction in which the clip slides.

In a first embodiment of the inventive self ligating orthodontic bracket, the arm tabs extend toward each other and a wedge locking ramp is located on the upper tie wing side of the bracket. The wedge locking ramp is located in a center of the slide path. The wedge locking ramp has a first or front surface facing toward the lower tie wings and extending up and away in an oblique manner relative to an upper surface of the slide path. A second or rear surface of the wedge locking ramp faces toward the upper tie wings and extends essentially orthogonally relative to the upper surface of the slide path. The front and rear surfaces of the wedge locking ramp are connected to each other by a transition region. Accordingly, when the clip is slid along the slide path from an open position toward a closed or locked position, that is, from the lower tie wings toward the upper tie wings, the front surface of the wedge locking ramp deflects the arm tabs of the clip vertically upward and away from, at an oblique angle relative to, the slide path and over the wedge locking ramp. Once the arm tabs are slid beyond the wedge locking ramp, the arm tabs return down onto the slide path wherein the arm tabs are locked behind the wedge locking ramp free of a transverse, coplanar or parallel locking force being exerted by the clip. The rear surface of the wedge locking ramp prevents the arm tabs from sliding toward the open position or the lower tie wings.

In a second embodiment of the inventive self ligating orthodontic bracket, a wedge locking ramp is located on the lower tie wing side of the bracket. Each arm also includes an inwardly extending locking tab located intermediate the free end of each arm and an opposing base end or body of the clip. The wedge locking ramp is located in a center of the slide path. The wedge locking ramp has a first or front surface facing toward the lower tie wings and extends up and away in an oblique manner relative to an upper surface of the slide path. A second or rear surface of the wedge locking ramp faces toward the upper tie wings and extends essentially orthogonally relative to the upper surface of the slide path. The front and rear surfaces of the wedge locking ramp are connected to each other by a transition region. Accordingly, when the clip is slid along the slide path from the open position to the closed or locked position, the front surface of the wedge locking ramp deflects the free end of each arm and inwardly extending locking tabs of the clip vertically upward and away from, at an oblique angle relative to, the slide path and over the wedge locking ramp. As the free ends of each arm approach or contact corresponding upper tie wings, the inwardly extending locking tabs are locked behind the wedge locking ramp free of a transverse, coplanar or parallel locking force being exerted by the clip. The rear surface of the wedge locking ramp prevents the inwardly extending locking tabs from sliding toward the open position or the lower tie wings. It is within the scope of the present invention for the second embodiment to be modified wherein an inwardly extending arm tab is provided at the free end of each arm.

In a third embodiment of the inventive self ligating orthodontic bracket, a wedge locking ramp is positioned on the left and right sides of the slide path. Each wedge locking ramp has a first or front surface facing toward the lower tie wings and extends up and away from an upper surface of the slide path. A second or rear surface of each wedge locking ramp faces toward the upper tie wings and extends essentially orthogonally relative to the upper surface of the slide path. The front and rear surfaces of each wedge locking ramp are connected to each other by a transition region. The wedge locking ramps are located on the upper tie wing side of the bracket.

It should be noted that the front surface of each wedge locking ramp may be perpendicular or orthogonal relative to the slide path. Alternatively, the front surface of each wedge locking ramp may be inclined relative to the slide path. A modification of the embodiment having the inclined front surfaces of the wedge locking ramps is to connect the wedge locking ramps with a beveled wall defined along a portion of the upper surface of the slide path between the wedge locking ramps, wherein the beveled wall facilitates the upward deflection of the arm tabs.

Accordingly, regardless of which configuration of the above-described wedge locking ramps is provided with the third embodiment, when the clip is slid along the slide path from an open position toward a closed or locked position, the front surface of each wedge locking ramp deflects a corresponding arm tab vertically upward and away from, at an oblique angle relative to, the slide path and over the wedge locking ramp. Once the arm tabs are slid beyond the wedge locking ramp, the arm tabs return down onto the slide path wherein the arm tabs are locked behind the wedge locking ramp free of a transverse, coplanar or parallel locking force being exerted by the clip. The rear surface of each wedge locking ramp prevents the corresponding arm tab from sliding toward the open position or the lower tie wings.

According to a fourth embodiment of the inventive self ligating orthodontic bracket, the slide path is slanted or angled downward relative to a bottom surface of the archwire slot and in a direction taken from the lower tie wings toward the upper tie wings. A protuberance is provided on the lower tie wing side of the slide path and positioned at the left and rights sides of the slide path. Each protuberance has a front, ramped surface. Moreover, the arm tabs are configured to span the archwire slot, and have a first surface abut against a front surface of the upper tie wing and possibly a second surface that abuts a rear, perpendicular surface of the protuberance that also defines part of the archwire slot. Accordingly, when the clip is slid along the slide path from an open position toward a closed or locked position, the front surface of each protuberance deflects a corresponding arm tab vertically upward and away from, at an oblique angle relative to, the slide path, over the protuberance, and across the archwire slot. Once the arm tabs are slid beyond the protuberance, a portion of the arm tabs rest on a part of the slide path located on the upper tie wing side of the bracket, and a remaining portion of the arm tabs span an opening of the archwire slot. The rear surface of the protuberance is abutted by the second surface of each arm tab wherein the arm tabs are locked behind the protuberance free of a transverse, coplanar or parallel locking force being exerted by the clip. The rear surface of each protuberance prevents the corresponding arm tab from sliding toward the open position or the lower tie wings.

In a fifth embodiment of the self ligating orthodontic bracket, as in the above-described third embodiment, a wedge locking ramp is positioned on the left and right sides of the slide path. Each wedge locking ramp has a first or front surface facing toward the lower tie wings and extends up and away from an upper surface of the slide path. A second or rear surface of each wedge locking ramp faces toward the upper tie wings and extends essentially orthogonally relative to the upper surface of the slide path. The front and rear surfaces of each wedge locking ramp are connected to each other by a transition region. The wedge locking ramps are located on the upper tie wing side of the bracket. Moreover, the front surface of each wedge locking ramp may be perpendicular or orthogonal relative to the slide path; inclined relative to the slide path; or have the wedge locking ramps connected to each other by a beveled wall defined along a portion of the upper surface of the slide path between the wedge locking ramps, wherein the beveled wall facilitates the upward deflection of the arm tabs.

However, in the fifth embodiment, guiding protuberances are provided on the upper and lower tie wing sides of the archwire slot and centrally located along the slide path. The protuberances deflect the arms of the clip upward or vertically at an oblique angle relative to the slide path or channel. When the clip is slid along the slide path from the open position toward a closed or locked position, the arm tabs are first deflected vertically by the lower guiding protuberance, then traverse the archwire slot, and are again deflected again vertically by the upper guiding protuberance. Once the arm tabs are deflected over the upper guiding protuberance, the arm tabs return down onto the slide path wherein the arm tabs are locked behind the wedge locking ramps free of a transverse, coplanar or parallel locking force being exerted by the clip. The rear surface of each wedge locking ramp prevents the corresponding arm tab from sliding toward the open position or the lower tie wings.

Furthermore, the inventive self ligating orthodontic bracket is configured to provide a low profile to minimize labial-lingual prominence. As noted above, the bracket includes a mounting base for attachment to a tooth surface, an archwire slot formed upon the base transversely oriented to the ties wings and sized for receiving an orthodontic archwire, a channel formed upon the base and transversely oriented to the archwire slot, and a ligating slide shape memory clip member slideably retained within stabilizing channels and closeable to capture or retain the archwire within the slot. The locking action for the arms of the shape memory sliding clip member may be based on the shape memory properties of the alloy and thermal activating properties at mouth temperature.

A convertible feature of the bracket allows the orthodontic professional to have the option of continuing to use the bracket as the treatment progresses towards the end without having to change brackets. The convertible feature also facilitates the orthodontist to use the instruments that the orthodontist normally uses every day during routine or normal procedures in order to convert the bracket. In addition to the convertability aspect, the clip on the inventive self ligating bracket allows the clip to easily be replaced in a simple, one step operation without having to remove or change the bracket.

Moreover, the inventive self ligating orthodontic convertible bracket includes a shape memory sliding clip member having improved fatigue resistance that withstands numerous opening and closing cycles and remains active and operational in the aggressive mouth environment throughout the orthodontic treatment. Preferably, the shape memory clip is manufactured from a Ni/Ti superelastic alloy by die stamping, chemically-etching, laser cut, or any other now-known or later developed process and provides such advantages as increased strength, flexibility, resilience, durability, reliability, shape memory, and the like.

Additional aspects and novel features relating to the present invention will be set forth in part in the description that follows, and in part will become more apparent to those skilled in the art upon examination of the following or upon learning by practice of aspects of the invention.

BRIEF DESCRIPTION OF THE DRAWINGS

The accompanying drawings, which are incorporated in and constitute part of this specification, illustrate embodiments of the invention and the detailed description of the embodiments serves to explain the principles and features of the invention.

DETAILED DESCRIPTION OF PREFERRED EMBODIMENTS

In the following detailed description, numerous specific details are set forth in order to provide a thorough understanding of the present invention. However, those skilled in the art will understand that the present invention may be practiced without these specific details, that the present invention is not limited to the depicted embodiments, and that the present invention may be practiced in a variety of alternate embodiments. In other instances, well known methods, procedures, components, and systems have not been described in detail.

Various operations will be described as multiple discrete steps performed in turn in a manner that is helpful for understanding the present invention. However, the order of description should not be construed as to imply that these operations are necessarily performed in the order they are presented, nor even order dependent.

Figure 1:
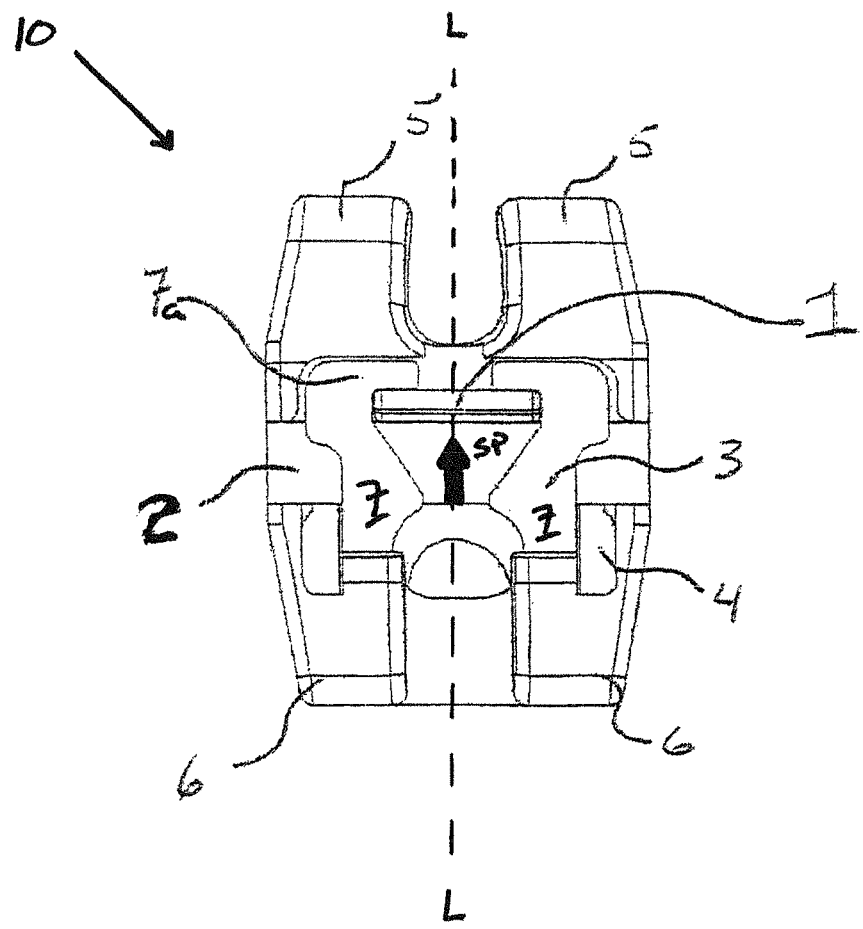
FIG. 1 is a plan view of a self ligating orthodontic bracket according to a first embodiment of the present invention, wherein the bracket and a sliding clip are in the closed or locked state.

FIG. 1 illustrates a plan view of a self ligating orthodontic bracket 10 according to a first embodiment of the present invention. The bracket 10 includes a bracket or housing 4 for attachment to the surface of a tooth, an archwire slot 2 defined by the housing 4 and configured to receive therein an archwire AW (FIG. 5), and a slidable ligating member or clip 3, illustrated in the closed or locked position, which retains the archwire AW in the archwire slot 2. The bracket 10 further includes a pair of upper tie wings 5 separated from a pair of opposing lower tie wings 6 by the archwire slot 2 defined therebetween.

It should be noted that the bracket 10 described herein, as well as any of the other embodiments of the inventive brackets, may have a base or lower surface configured to have a compound radius which may better adapt to the surface of the tooth.

Moreover, in the first embodiment as well as any of the later discussed embodiments, at least one of the upper tie wings 5 and the lower tie wings 6 may be integrally formed with the housing 4 or as a separate component that is attached thereto. The components of the bracket 10 may be formed from any known or later developed manufacturing technique, such as by injection molding, die stamping, etching, laser cutting, milling, die casting, sintering, machining, microcasting and the like. Further, it is within the scope of the invention for when such components are separate and distinct from each other to be joined together using any known or later developed manufacturing technique such as using an adhesive, ultrasonic welding, and the like. Biocompatible metallic alloys, composite material, and ceramics are materials from which at least one and preferably all of the components of the inventive bracket may be manufactured.

The clip 3 is configured to travel within a slide path SP defined by the upper and lower ties wings 5 and 6, respectively, in a direction that extends from the lower tie wings 6 to the upper tie wings 5 and which is transverse relative to the direction in which the archwire slot 2 extends. The clip 3 is preferably manufactured from a shape memory material and includes a pair of arms 7, each arm may have a tab 7a extending from a free end of the arm 7 in a direction that is generally parallel to the archwire slot 2 and transverse to the direction in which the clip 3 slides.

In the unlocked state (FIGS. 2-4), the clip 3 does not cover the archwire slot 2 as the tabs 7a of each arm 7 are located on the lower tie wing side of the archwire slot 2. The clip 3 travels along the slide path SP from the unlocked state or position to a locked state or position (FIGS. 1 and 5-6) wherein the tabs 7a of each arm 7 are positioned on the upper tie wing side of the archwire slot 2. As clearly illustrated in FIGS. 1 and 5-6, the tabs 7a of each arm 7 are located between the upper tie wings 5 and a wedge locking ramp 1 positioned within the slide path SP along which the clip 3 travels when going from the unlocked state or position to the locked state or position.

Similarly, in the first embodiment as well as any of the later discussed embodiments, the wedge locking ramp 1 may be integrally formed with the housing 4 or as a separate component that is attached thereto. The wedge locking ramp 1 may be formed from any known or later developed manufacturing technique, such as those listed above. Further, it is within the scope of the invention for when the wedge locking ramp 1 is a separate and distinct component relative to the other components of the housing 4, the wedge locking ramp 1 can be joined to the housing 4 using any known or later developed manufacturing technique such as using an adhesive, ultrasonic welding, snap fit, and the like. For example, it is envisioned that the housing 4 may have peg holes defined therein that can engage and securely retain therein pegs or other such projections that are configured to be engaged by the peg holes and retained therein.

In the first embodiment of the invention, the wedge locking ramp 1 is positioned substantially within the center of the slide path SP and at least on a longitudinal axis L of the slide path SP extending from the lower tie wings 6 to the upper ties wings 5.

Figure 3:
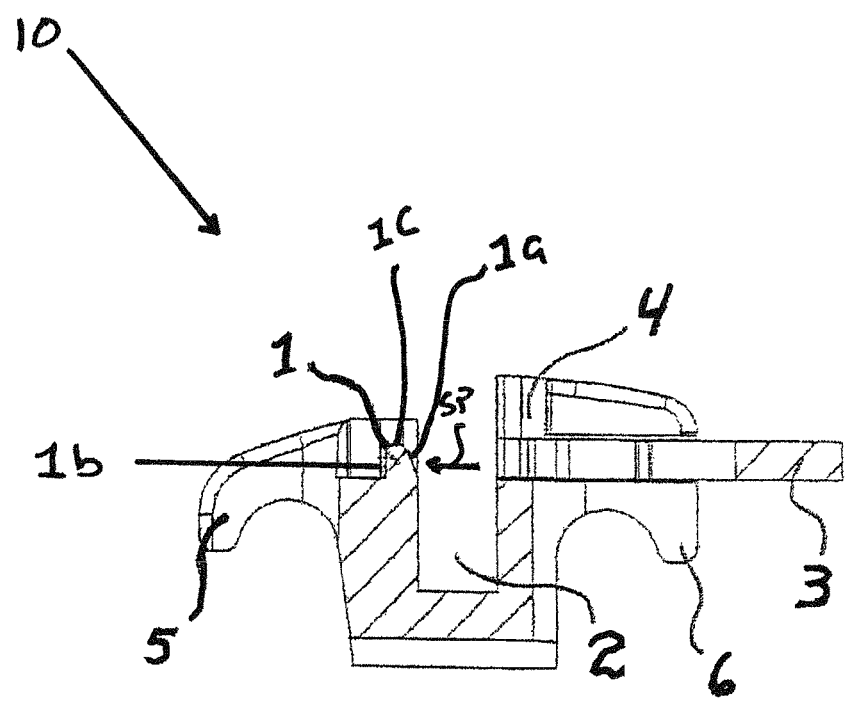
FIG. 3 is a cross-sectional view of the self ligating orthodontic bracket illustrated in FIG. 2.
Figure 4:
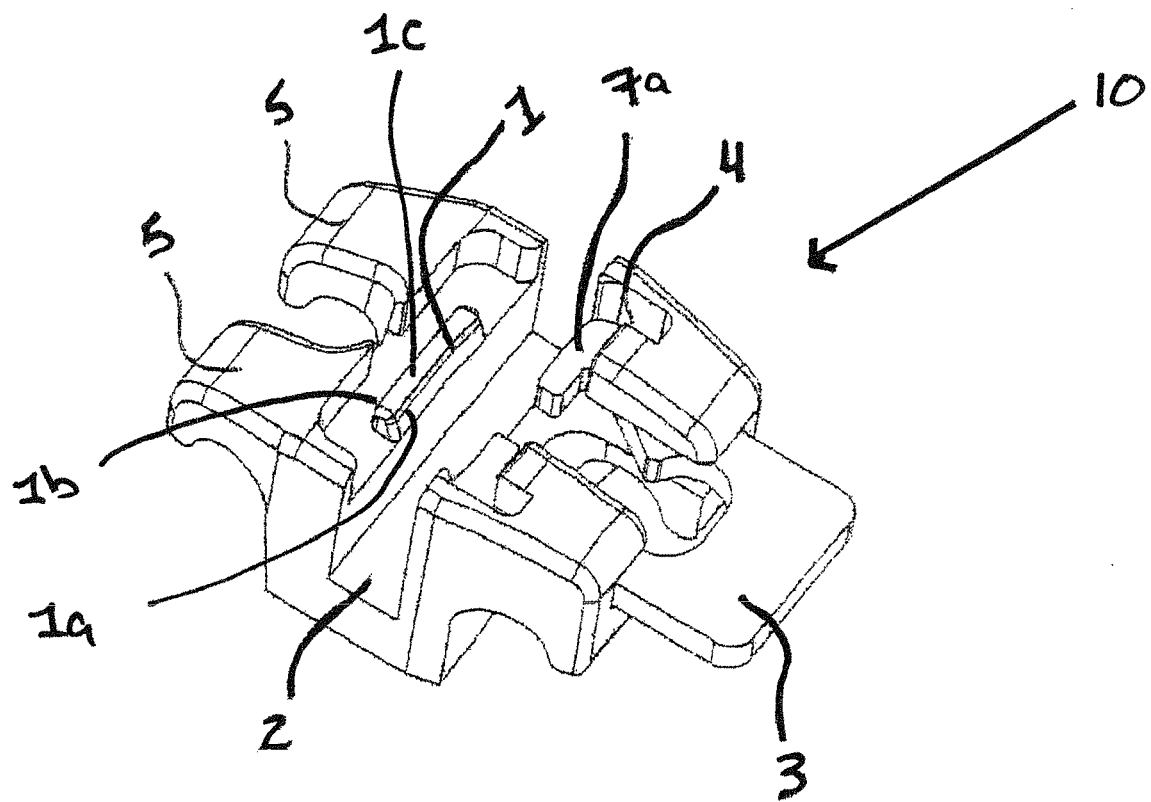
FIG. 4 is a perspective view of the self ligating orthodontic bracket illustrated in FIG. 2.
Figure 5:
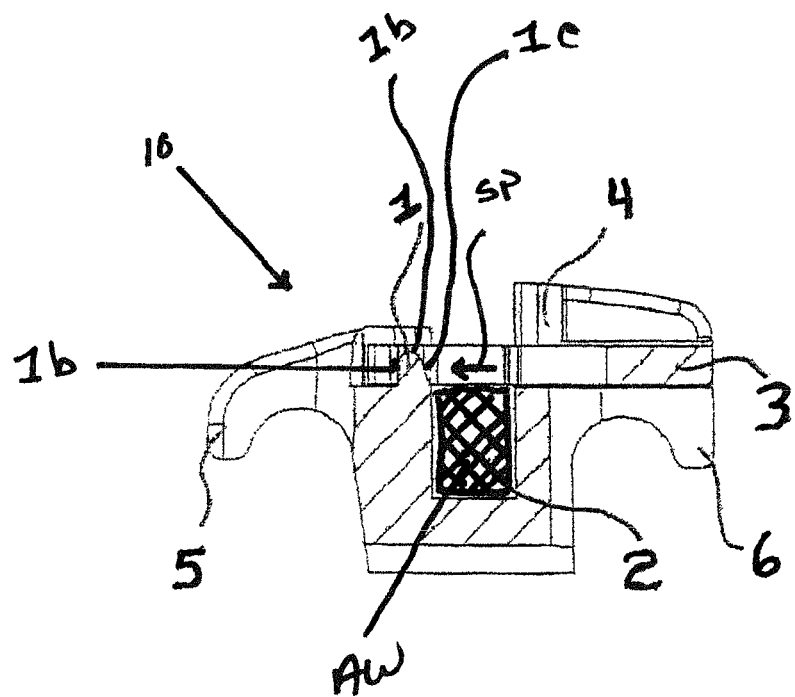
FIG. 5 is a cross-sectional view of the self ligating orthodontic bracket illustrated in FIG. 1.

As shown best in FIGS. 3-5, the wedge locking ramp 1 has a first or front surface 1a facing toward the lower tie wings 6 and extending up and away in an oblique manner relative to an upper surface of the slide path SP. A second or rear surface 1b of the wedge locking ramp 1 faces toward the upper tie wings 6 and extends essentially orthogonally relative to the upper surface of the slide path SP. The front surface 1a and rear surface 1b of the wedge locking ramp 1 are connected to each other by a transition surface 1c, which is preferably, but not limited to, arcuate in shape.

Accordingly, an orthodontic professional would position and retain the archwire AW within the archwire slot 2 of the bracket 10 as follows.

Figure 2:
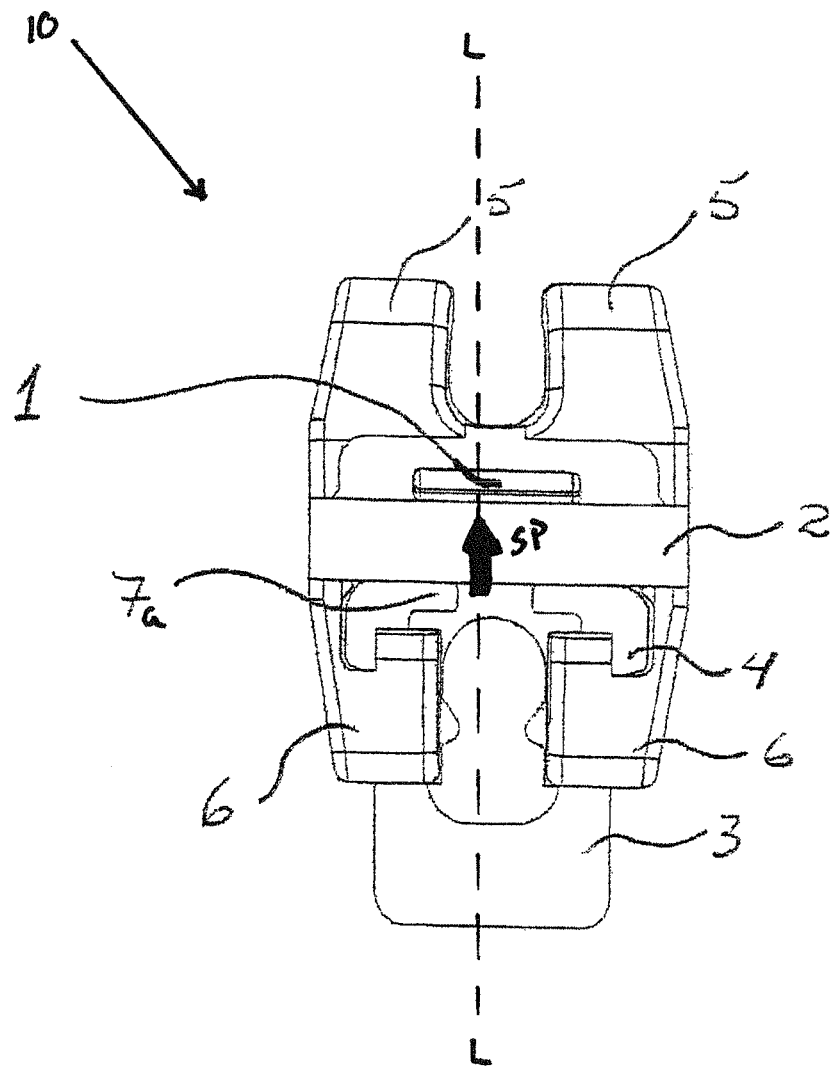
FIG. 2 is a plan view of the self ligating orthodontic bracket illustrated in FIG. 1, wherein the bracket and a sliding clip are in the open or unlocked state.

First, as shown in FIG. 2, in the unlocked state, the clip 3 is slid along the slide path SP starting from the lower tie wings 6 in a direction toward the upper tie wings 5. That is, the tabs 7a of each arm 7 of the clip 3 are located on the lower tie wing side of the archwire slot 2 such that the archire slot 2 is exposed to the orthodontic professional. As shown in the FIG. 3, which is a cross-sectional view of the plan view illustrated in FIG. 2, and FIG. 4, which is a perspective view of the plan view illustrated in FIG. 2, the tabs 7a do not completely span or otherwise totally block the archire slot 2, thereby providing the orthodontic professional with sufficient access to the slot 2 to position the archwire AW within the slot 2.

Figure 6:
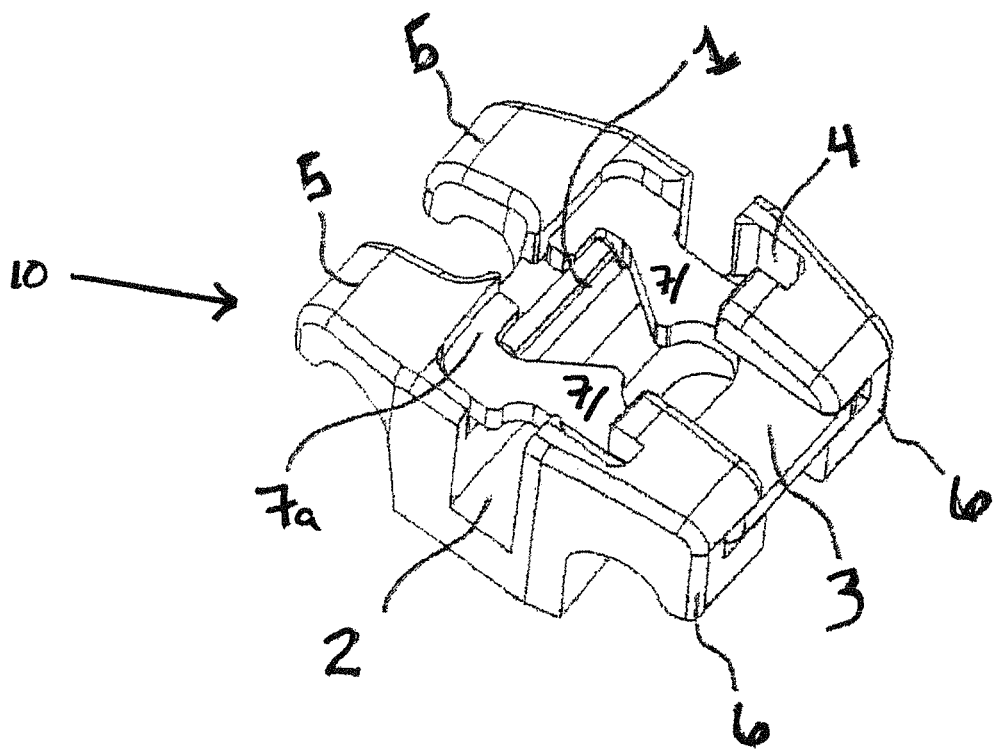
FIG. 6 is a perspective view of the self ligating orthodontic bracket illustrated in FIG. 1.

Once the archwire AW is positioned within the archwire slot 2, the clip 3 is slid further along the slide path SP to fully span the slot 2 and go from the unlocked or open state to the locked or closed state, that is, from the lower tie wings 6 toward the upper tie wings 5, wherein the front surface 1a of the wedge locking ramp 1 deflects each tab 7a of each arm 7 of the clip 3 vertically or at least obliquely upward and away from, at an oblique angle relative to, the upper surface of the slide path SP and over the wedge locking ramp 1. Once the tabs 7a of each arm 7 are slid beyond the wedge locking ramp 1, the tabs 7a return down onto the slide path SP wherein the tabs 7a are positioned between the wedge locking ramp 1 and the upper tie wings 6, as shown in the cross-sectional view of FIG. 5 and the perspective view of same, which is shown in FIG. 6. The tabs 7a are locked or secured by the wedge locking ramp 1 free of any transverse, coplanar or parallel locking force being exerted by the clip 3. Rather, the rear surface 1b of the wedge locking ramp 1 prevents the tabs 7a from sliding toward the lower tie wings 6 and to the open or unlocked position. Moreover, as shown in FIG. 5, the tabs 7a of each arm 7 are sized and configured so to engage the rear surface 1b of the wedge locking ramp 1. Although FIG. 5 illustrates the tabs 7a are free of contacting the upper tie wings 5 when in the locked state as evidenced by a gap or space defined between the tabs 7a and the upper tie wings 5, it is within the scope of the invention for the tabs 7a to be sized and configured to physically contact or engage the rear surface 1b of the wedge locking ramp 1 and a surface of the upper tie wings 5 which opposes the rear surface 1b such that the tabs 7a are securely or tightly maintained therebetween.

Figure 7:
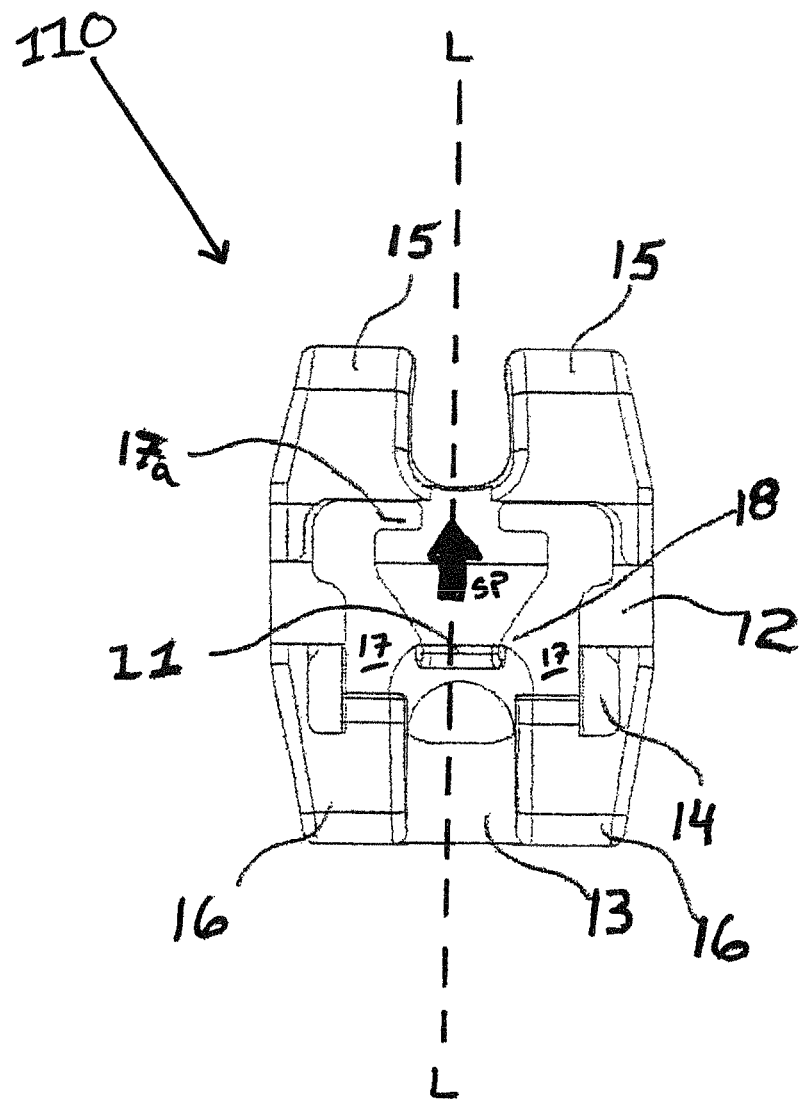
FIG. 7 is a plan view of a self ligating orthodontic bracket according to a second embodiment of the present invention, wherein the bracket and a sliding clip are in the closed or locked state.

FIG. 7 illustrates a plan view of a self ligating orthodontic bracket 110 according to a second embodiment of the present invention.

The bracket 110 includes a self ligating orthodontic bracket or housing 14 for attachment to the surface of a tooth, an archwire slot 12 defined by the housing 14 and configured to receive therein the archwire AW, and a slidable ligating member or clip 13 illustrated in the closed or locked position which retains the archwire AW in the archwire slot 12. The bracket 110 further includes a pair of upper tie wings 15 separated from a pair of opposing lower tie wings 16 by the archwire slot 12 defined therebetween.

The clip 13 is configured to travel within the slide path SP defined by the upper and lower ties wings 15 and 16, respectively, in a direction that extends from the lower tie wings 16 to the upper tie wings 15 and which is transverse relative to the direction in which the archwire slot 12 extends. The clip 13 is preferably manufactured from a shape memory material. The clip 13 includes a pair of arms 17, and like the arms 7 of the first embodiment, each arm 17 of the second embodiment may optionally have a tab 17a extending from a free end of the arm 17 in a direction that is generally parallel to the archwire slot 12 and transverse to the direction in which the clip 13 slides. Moreover, each arm 17 also includes an inwardly extending locking tab 18 located intermediate a base of the clip 13 and a free end of each arm 17 taken in a direction extending from the lower tie wings 16 toward the upper tie wings 15. Accordingly, while the tabs 17a are optional structural components of the arms 17 in the second embodiment of the invention, the inwardly extending locking tabs 18 are affirmatively provided therewith.

Furthermore, the locking tabs 18 of each arm 17 extend toward the locking tab 18 of the other arm 17. The locking tabs 18 may be configured to resemble any known or later developed geometric shape so long as the tabs 18 are able to engage and be retained by a wedge locking ramp 11 discussed below.

Also, while the inwardly extending locking tabs 18 are preferably manufactured to be integral with the remainder of the clip 13, it is within the scope of the invention for the tabs 18 to be formed as separate and distinct components from the remainder of the clip 13, wherein the locking tabs 18 are attached or otherwise affixed to a corresponding arm 17 using any known or later developed technique, such as, by using an adhesive, ultrasonic welding, snap fit and the like.

In the unlocked state (FIGS. 8-10), the clip 13 does not cover the archwire slot 12 as the inwardly extending locking tabs 18 of each arm 17 are located on the lower tie wing side of the archwire slot 12. The clip 13 travels along the slide path SP from the unlocked state or position to a locked state or position (FIGS. 7 and 11-12) wherein the locking tabs 18 of each arm 17 are positioned on the upper tie wing side of the archwire slot 12.

Figure 11:
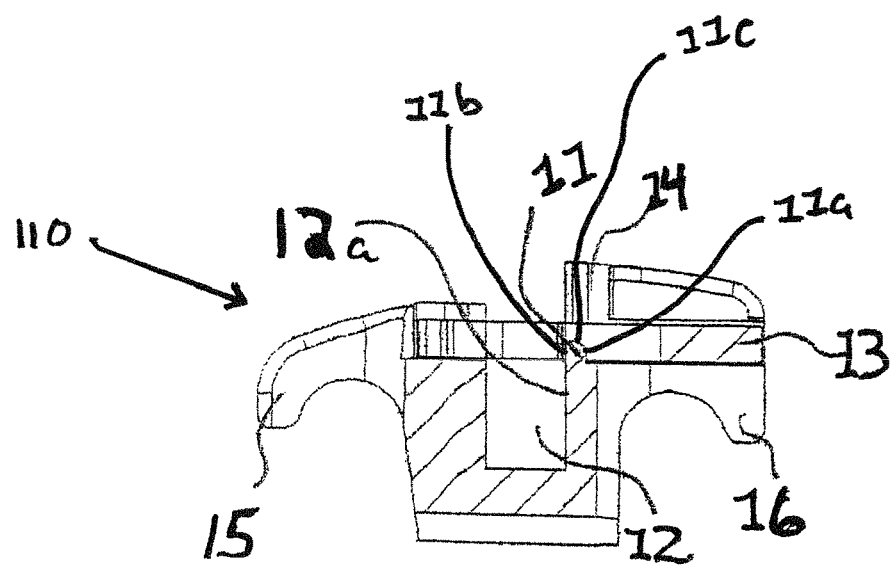
FIG. 11 is a cross-sectional view of the self ligating orthodontic bracket illustrated in FIG. 7.
Figure 12:
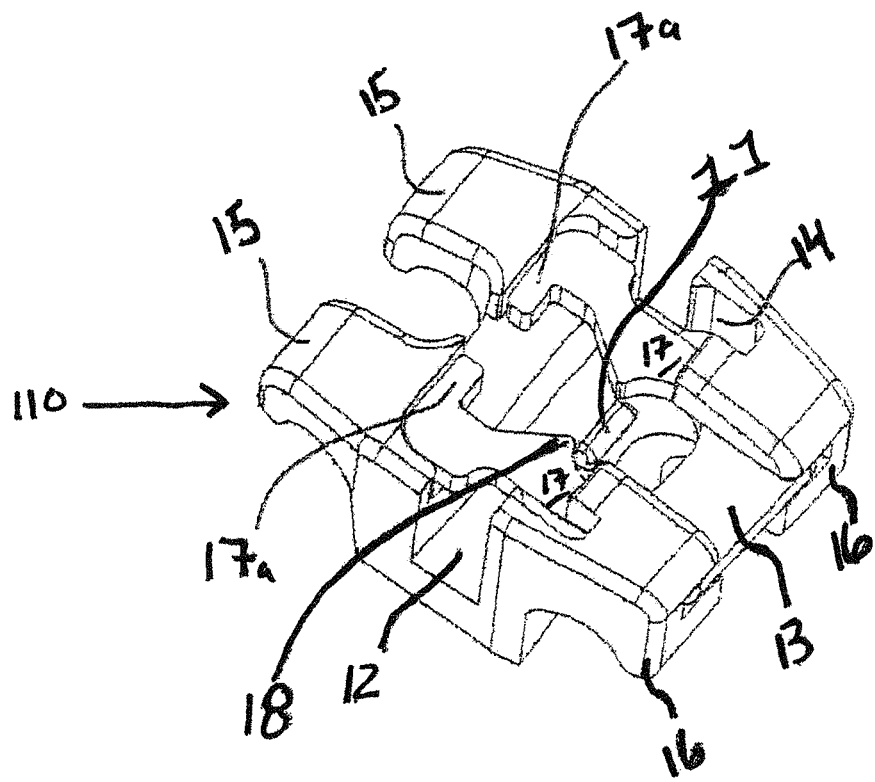
FIG. 12 is a perspective view of the self ligating orthodontic bracket illustrated in FIG. 7.

In the locked state, as clearly illustrated in FIGS. 7 and 11-12, the inwardly extending locking tabs 18 of each arm 17 are located between the upper tie wings 15 and the wedge locking ramp 11 positioned within the slide path SP along which the clip 13 travels when going from the unlocked state or position to the locked state or position.

In the second embodiment of the invention, the wedge locking ramp 11 is positioned substantially within the center of the slide path SP and at least on a longitudinal axis L of the slide path SP extending from the lower tie wings 16 to the upper ties wings 15. Moreover, the wedge locking ramp 11 is located on the lower tie wing side of the archwire slot 12.

Figure 9:
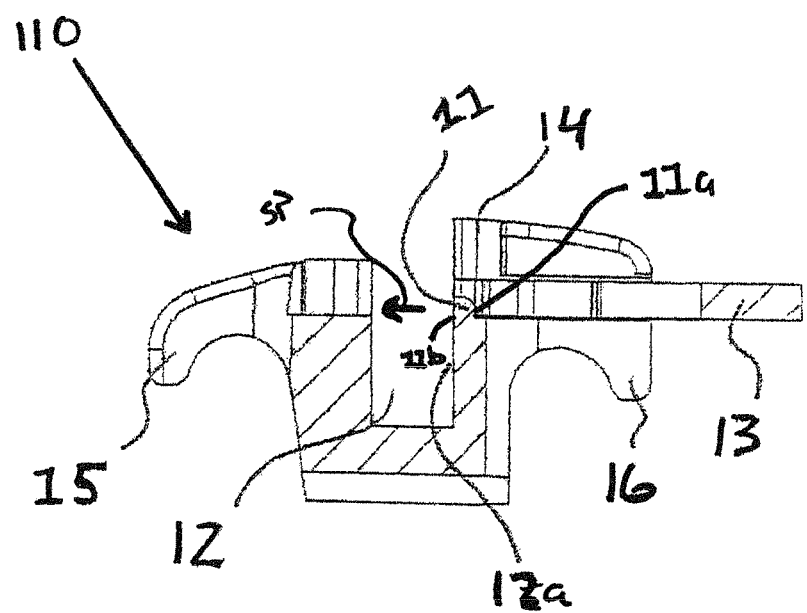
FIG. 9 is a cross-sectional view of the self ligating orthodontic bracket illustrated in FIG. 8.
Figure 10:
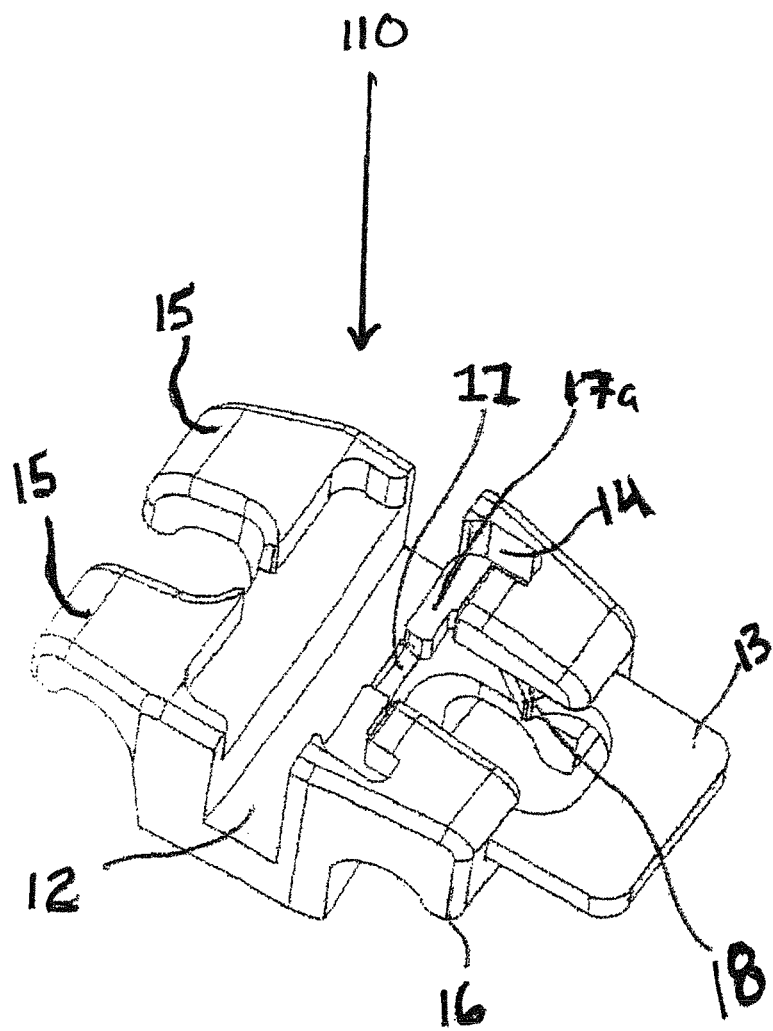
FIG. 10 is a perspective view of the self ligating orthodontic bracket illustrated in FIG. 8.

As shown best in FIGS. 9 and 11, the wedge locking ramp 11 has a first or front surface 11a facing toward the lower tie wings 16 and extending up and away in an oblique manner relative to an upper surface of the slide path SP. A second or rear surface 11b of the wedge locking ramp 11 faces toward the upper tie wings 16 and extends essentially orthogonally relative to the upper surface of the slide path SP. It is within the scope of the invention for the rear surface 11b of the wedge locking ramp 11 to form a continuous surface of a first upwardly extending wall 12a of the archwire slot 12, as clearly shown in FIG. 9.

However, it is also within the scope of the invention for the wedge locking ramp 11 to be positioned between the archwire slot 12 and lower tie wings 16 such that the rear surface 11b of the wedge locking ramp 11 is separate and distinct from the first upwardly extending wall 12a of the archwire slot 12 in a manner wherein an upper surface of the slide path SP along which the clip 13 travels is disposed between the rear surface 11b of the wedge locking ramp 11 and the archwire slot 12.

Preferably, the front surface 11a and rear surface 11b of the wedge locking ramp 11 are connected to each other by a transition surface 11c, which may be arcuate or any other suitable geometric configuration.

Accordingly, an orthodontic professional would position and retain the archwire AW within the archwire slot 12 of the bracket 110 as follows.

Figure 8:
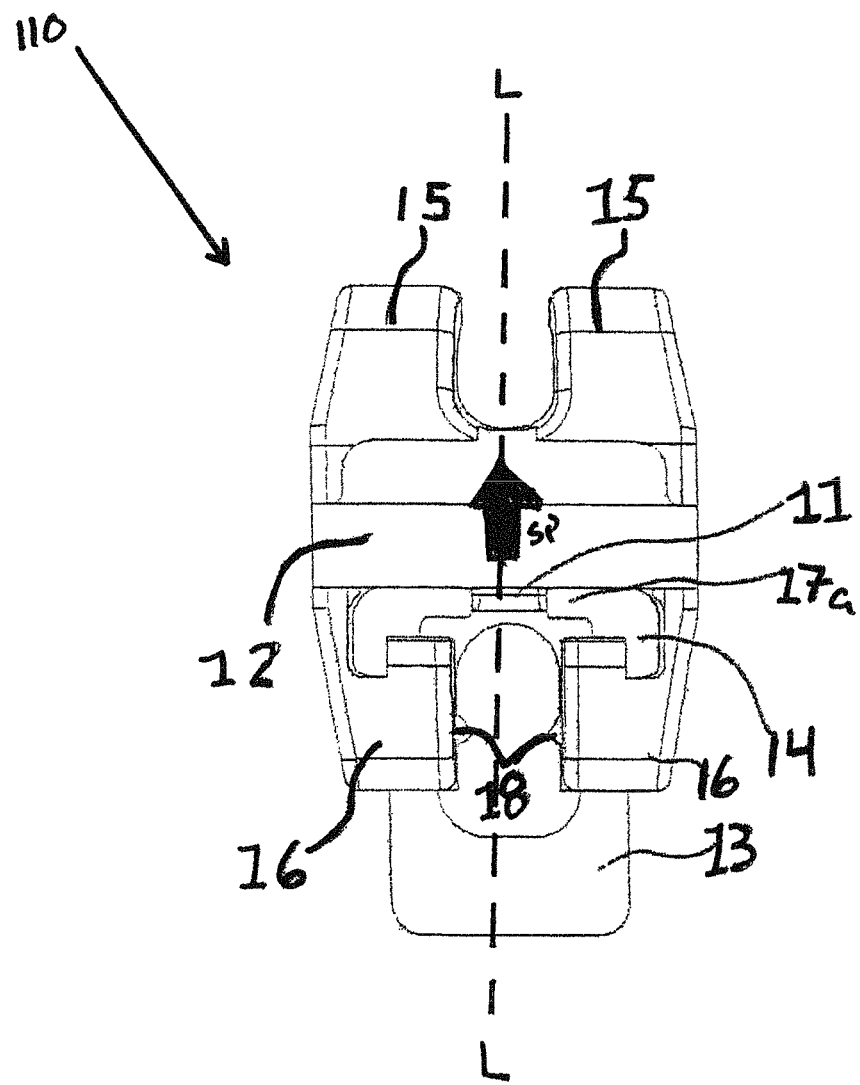
FIG. 8 is a plan view of the self ligating orthodontic bracket illustrated in FIG. 7, wherein the bracket and a sliding clip are in the open or unlocked state.

First, as shown in FIG. 8, in the unlocked state, the clip 13 is slid along the slide path SP starting from the lower tie wings 16 in a direction toward the upper tie wings 15. That is, the inwardly extending locking tabs 18 of each arm 17 of the clip 13 are located on the lower tie wing side of the archwire slot 12 such that the archire slot 12 is exposed to the orthodontic professional. As shown in the FIG. 9, which is a cross-sectional view of the plan view illustrated in FIG. 8, and FIG. 10, which is a perspective view of the plan view illustrated in FIG. 8, the free ends of the arms 17 do not completely span or otherwise totally block the archire slot 12, thereby providing the orthodontic professional with sufficient access to the slot 12 to position the archwire AW within the slot 12.

Once the archwire AW is positioned within the archwire slot 12, the clip 13 is slid further along the slide path SP, wherein the arms 17 fully span the slot 12, from the unlocked or open state to the locked or closed state, that is, from the lower tie wings 16 toward the upper tie wings 15, wherein the front surface 11a of the wedge locking ramp 11 deflects each inwardly extending locking tab 18 of each arm 17 of the clip 13 vertically or at least obliquely upward and away from, at an oblique angle relative to, the upper surface of the slide path SP and over the wedge locking ramp 11. Once the locking tabs 18 of each arm 17 are slid beyond the wedge locking ramp 11, the locking tabs 18 return down onto the slide path SP wherein the locking tabs 18 are positioned between the wedge locking ramp 11 and the upper tie wings 16, as shown in the cross-sectional view of FIG. 11 and the perspective view of same, which is shown in FIG. 12. The inwardly extending locking tabs 18 are locked or secured by the wedge locking ramp 11 free of any transverse, coplanar or parallel locking force being exerted by the clip 13, thereby securely retaining the archwire AW within the slot 12. That is, the rear surface 11b of the wedge locking ramp 11 prevents the locking tabs 18 from sliding toward the lower tie wings 16 and to the open or unlocked position. Moreover, as shown in FIGS. 7 and 11-12, the locking tabs 18 of each arm 17 are sized and configured so to engage the rear surface 11b of the wedge locking ramp 11.

Figure 13:
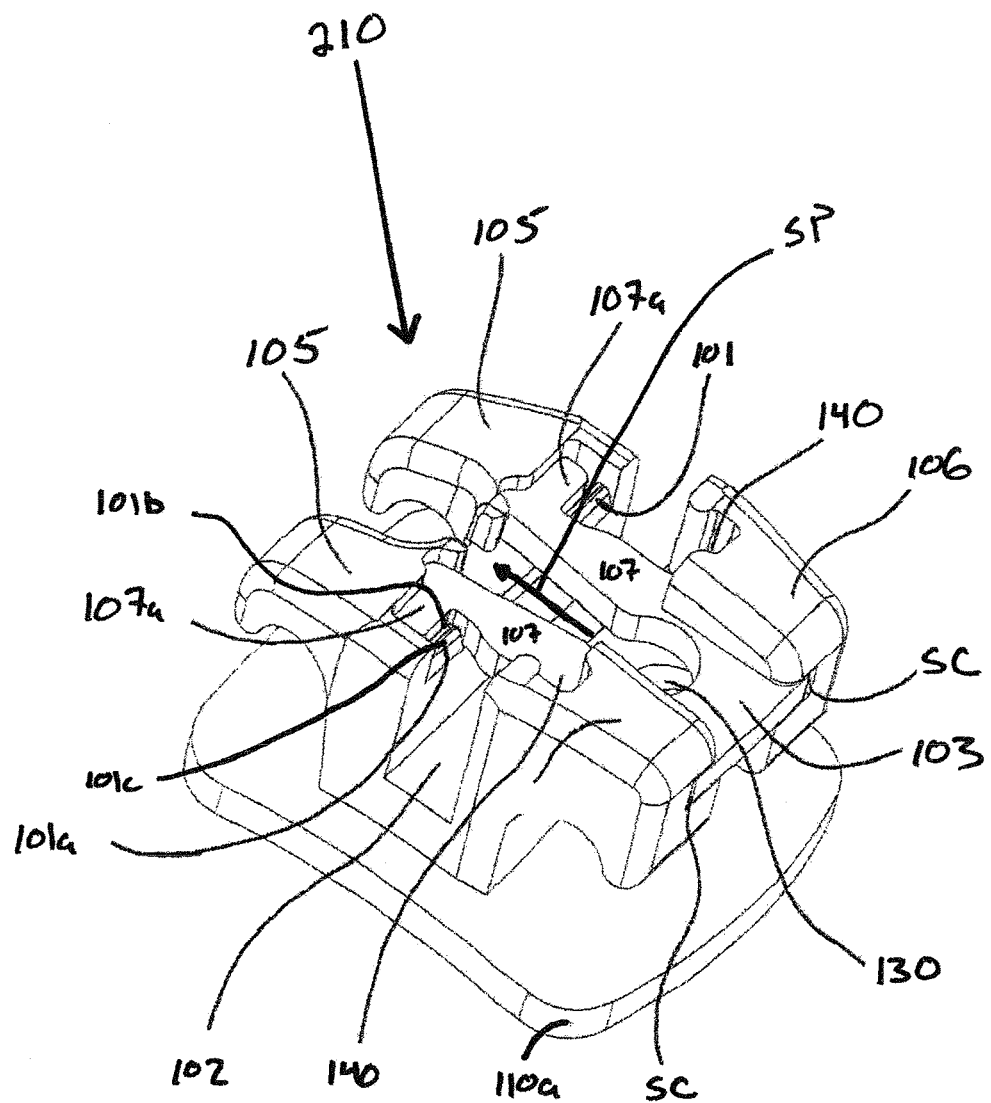
FIG. 13 is a perspective view of a self ligating orthodontic bracket according to a third embodiment of the present invention, wherein the bracket and a sliding clip are in the closed or locked state.

FIG. 13 illustrates a perspective view of a self ligating orthodontic bracket 210 according to a third embodiment of the present invention.

The bracket 210 includes a bracket base 110a for attachment to the tooth surface, an archwire slot 102 configured to receive therein an archwire AW, and a slidable ligating member or clip 103 which retains the archwire AW in the archwire slot 102. The clip 103, like clips 3 and 13 of the first and second embodiments, can be selectively manipulated from the closed or locked state illustrated in FIG. 13 to the open or unlocked state, thereby exposing the archwire slot 102 extending transversely relative to the slide path SP traveled by the clip 103 in order to permit the orthodontic professional to place the archwire AW within the slot 102. The bracket 210 further includes a pair of upper tie wings 105 separated from a pair of opposing lower tie wings 106 by the archwire slot 102 defined therebetween.

The clip 103 is configured to travel along the slide path SP defined by the upper and lower ties wings 105 and 106, respectively, in a direction that extends from the lower tie wings 106 to the upper tie wings 105 and which is transverse relative to the direction in which the archwire slot 102 extends. The clip 103 is preferably manufactured from a shape memory material and includes a pair of arms 107, each arm having a tab 107a extending from a free end of the arm 107 in a direction that is generally parallel to the archwire slot 102 and transverse to the direction in which the clip 103 slides.

However, unlike in the first embodiment where the tabs 7a extend toward each other, the tabs 107a of the third embodiment extend away from each other such that the tabs 107a extend away from the longitudinal axis of the slide path SP which extends from the lower tie wings 106 toward the upper tie wings 105.

Furthermore, the clip 103 slides along the slide path SP and within a slide channel SC defined by distal and mesial walls of the lower tie wings 105 and oriented transversely relative to the archwire slot 102. Put another way, the distal and mesial walls extend orthogonally relative to the archwire slot 102 or parallel relative to the longitudinal axis of the slide path SP.

In the unlocked state, the clip 103 does not cover the archwire slot 102 as the tabs 107a of each arm 107 are located on the lower tie wing side of the archwire slot 102. The clip 103 travels along the slide path SP from the unlocked state or position to a locked state or position wherein the tabs 107a of each arm 107 are positioned on the upper tie wing side of the archwire slot 102. As clearly illustrated in FIG. 13, the tabs 107a of each arm 107 are located between the upper tie wings 105 and a wedge locking ramp 101 positioned on the left and rights sides of the slide path SP along which the clip 103 travels when going from the unlocked state or position to the locked state or position.

In the third embodiment of the invention, a wedge locking ramp 101 is positioned on the left and right sides of the slide path SP on the upper tie wing side of the bracket 210. Each wedge locking ramp 101 has a first or front surface 101a facing toward the lower tie wings 106 and extending up and away from an upper surface of the slide path SP. A second or rear surface 101b of the wedge locking ramp 101 faces toward the upper tie wings 106 and extends essentially orthogonally relative to the upper surface of the slide path SP. The front surface 101a and rear surface 101b of the wedge locking ramp 101 are connected to each other by a transition surface 101c.

Figure 14:
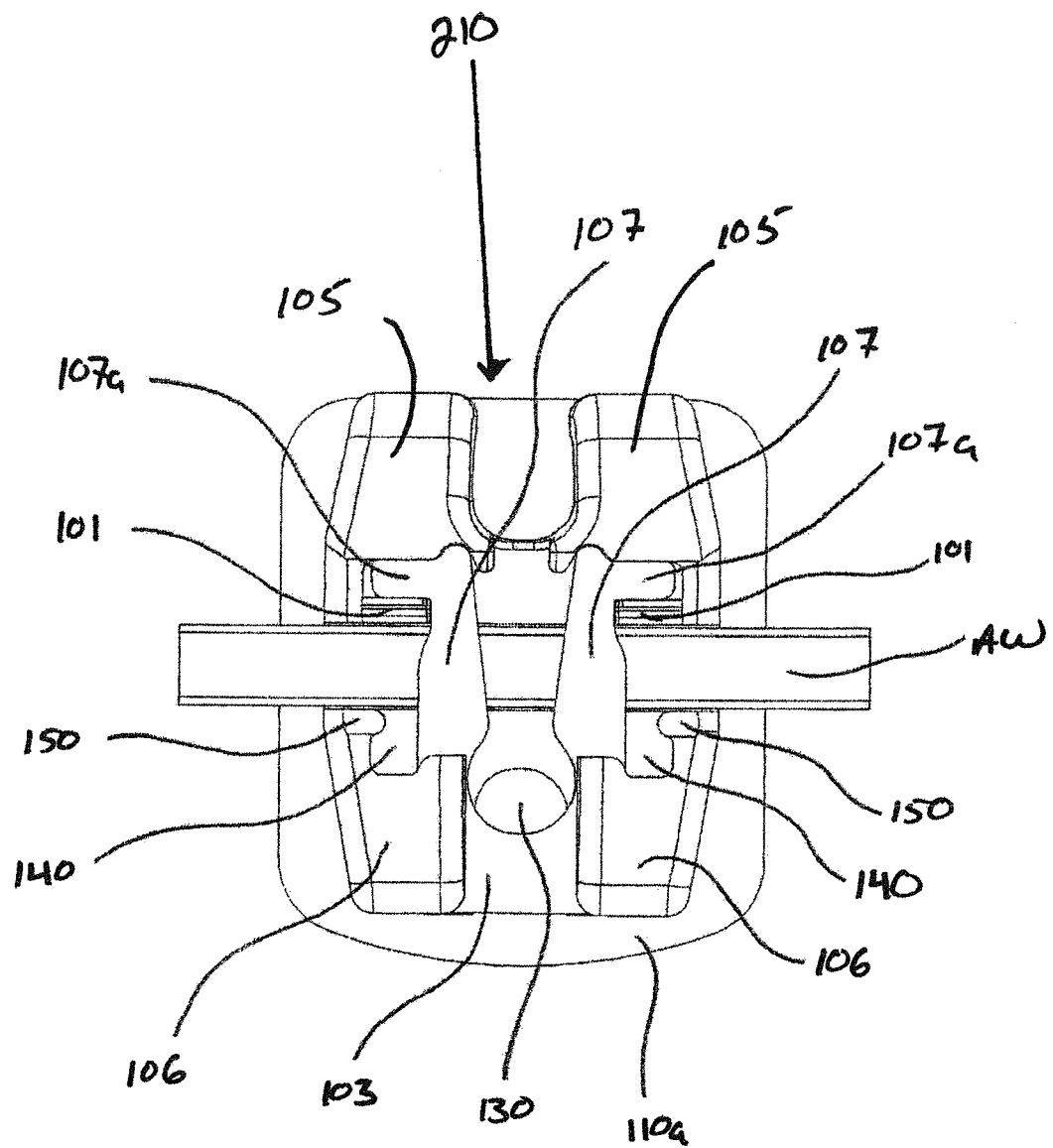
FIG. 14 is a plan view of the self ligating orthodontic bracket illustrated in FIG. 13.
Figure 15:
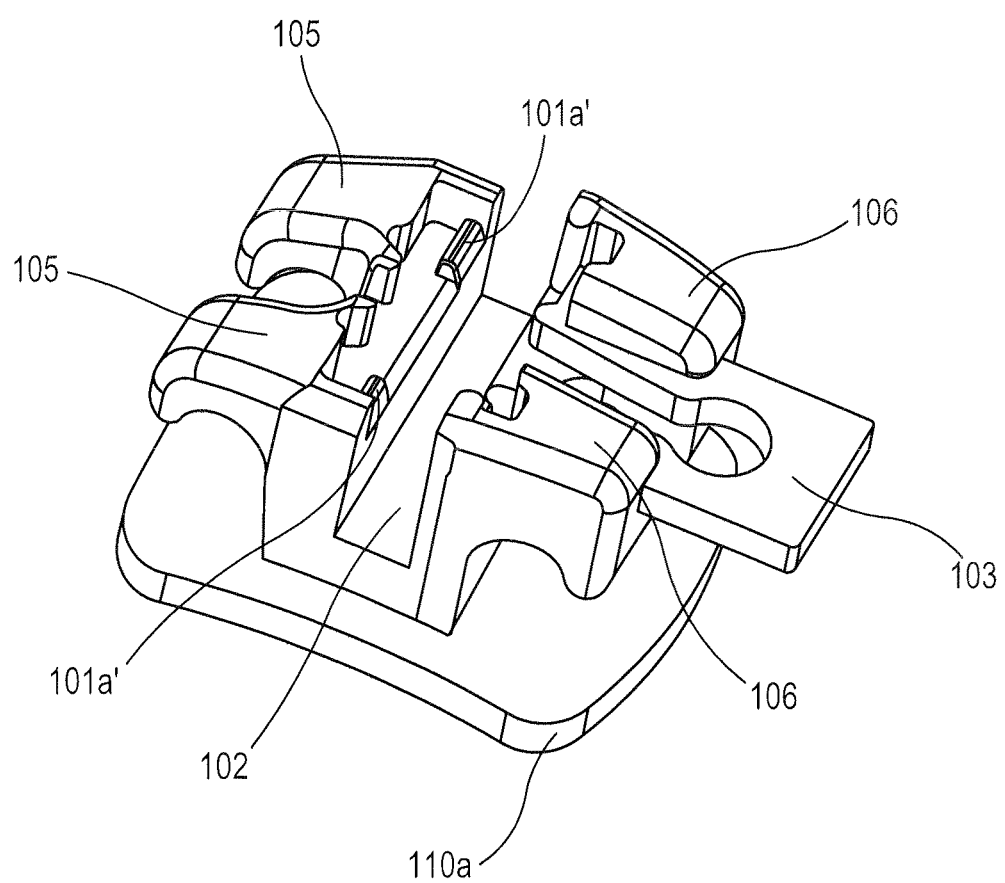
FIG. 15 is a perspective view of the self ligating orthodontic bracket illustrated in FIG. 13, wherein the bracket and a sliding clip are in the open or unlocked state.
Figure 16:
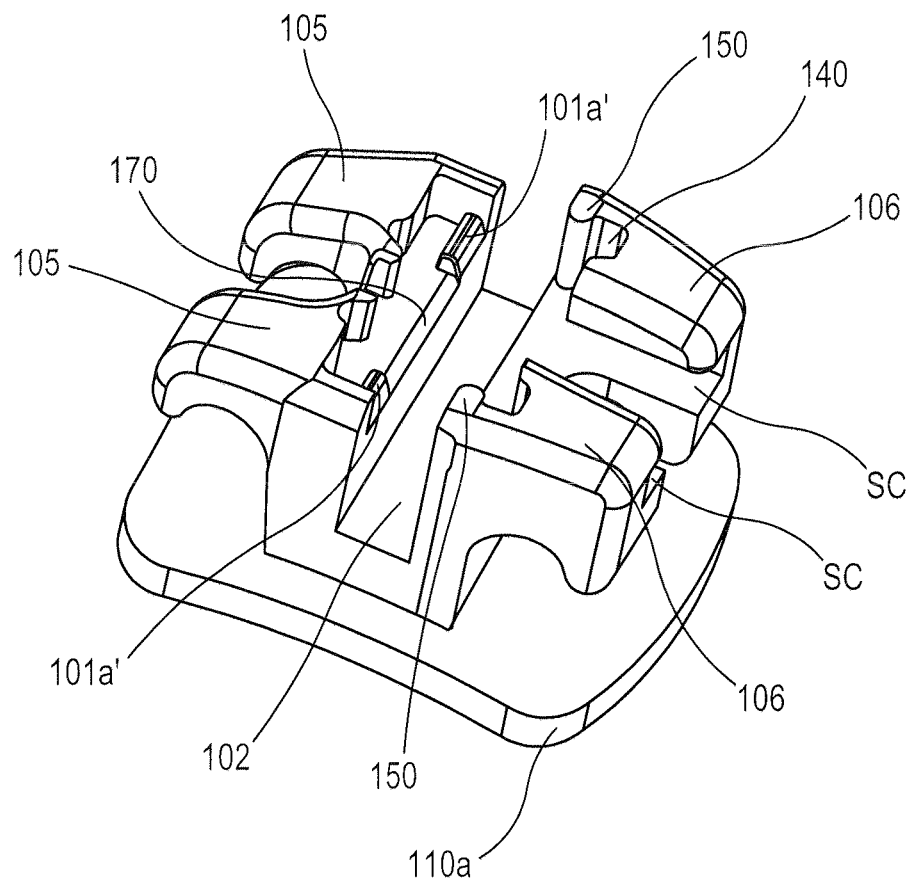
FIG. 16 is a perspective view of a self ligating orthodontic bracket according to a modified version of the third embodiment of the present invention.
Figure 17:
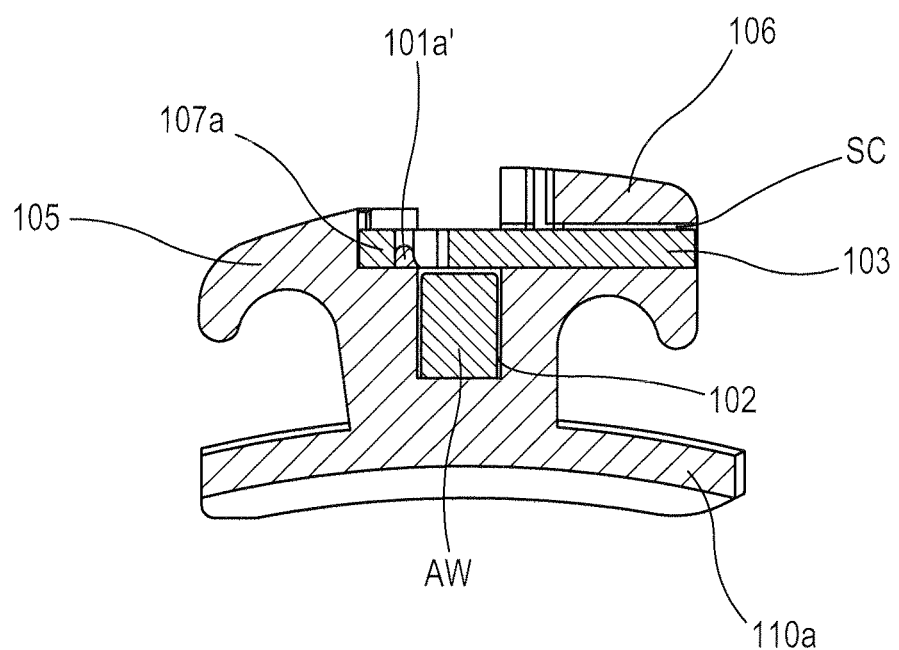
FIG. 17 is a cross-sectional view of the self ligating orthodontic bracket illustrated in FIG. 16, wherein the sliding clip is in the closed or locked state with the bracket.
Figure 18:
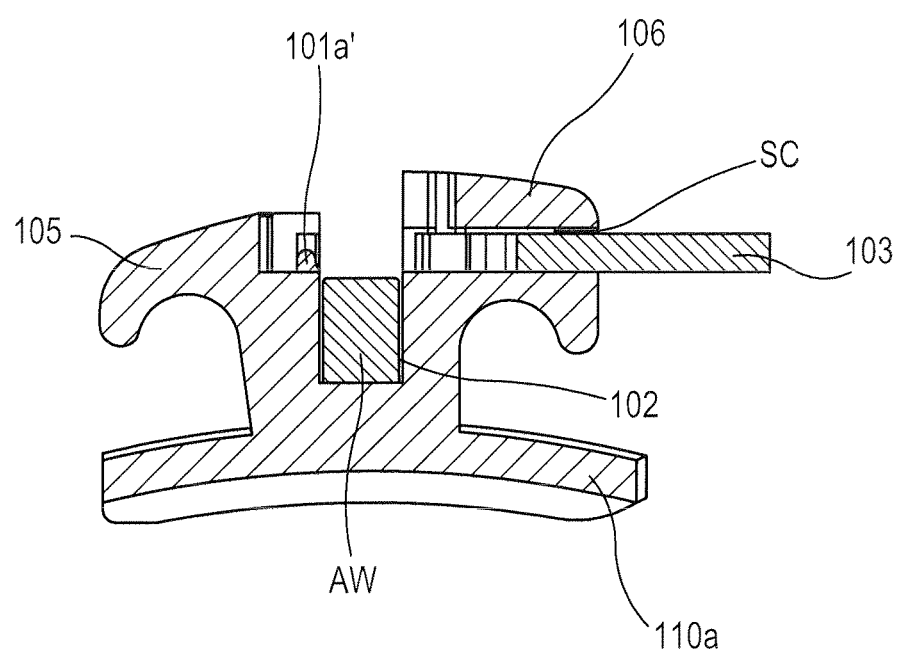
FIG. 18 is a cross-sectional view of the self ligating orthodontic bracket illustrated in FIG. 16, wherein the bracket and a sliding clip are in the open or unlocked state.

It is within the scope of the invention for the front surface 101a of each wedge locking ramp 101 of the third embodiment to be orthogonal or perpendicular relative to the slide path SP, as illustrated in FIGS. 13 and 14 herein. Alternatively, as shown in FIG. 15, the front surface 101a' of the wedge locking ramp 101 may be inclined relative to the slide path SP with a beveled surface. A modification of the embodiment illustrated in FIG. 15 is to connect the wedge locking ramps 101, 101 with a beveled wall 170 defined along a portion of the upper surface of the slide path SP between the wedge locking ramps 101, 101, wherein the beveled wall 170 facilitates the upward deflection of the arm tabs 107a. The modification of the embodiment illustrated in FIG. 15 is provided in FIGS. 16-18.

As noted above, each version of the third embodiment includes a wedge locking ramp 101, 101 on the left and rights sides of the slide path SP.

Moreover, in addition to comprising the slide channel SC, each bracket 1, 110 and 210, including those described later, may further optionally include a coplanar locking recess 140 defined by the lower tie wings 6, 16, and 106, for example, that is used to lock the tabs 7a, 17a, and 107a of the clip 3, 13, and 103 in the open or unlocked state. A circular opening 130 defined by an open area defined between the arms 7, 7, 17, 17 and 107, 107 of the clip 3, 13, and 103, and the first upwardly extending wall 12a of the archwire slot 2, 12, and 102. An orthodontic tool such as, fore example, an explorer can be inserted into the circular opening 130 and with a lever motion rotation of approximately 45° relative to the slide path SP, will disengage the clip 3, 13 and 103 from the wedge locking ramps 1, 11, and 101 described above, as well as those discussed later herein, thereby exposing the archwire slot 2, 12, 102 to the orthodontic professional.

Turning to the embodiment illustrated in FIG. 14, which for the following discussion is an exemplary embodiment of the bracket illustrated in FIGS. 13-18, the archwire AW is clearly shown as being captured or securely retained in the archwire slot 102 by the clip 103 in the closed or locked state. The clip 103 includes the tabs 107a engaging and securely retained by the rear surface 101b of the wedge locking ramps 101, 101. The tabs 107a, 107a are positioned between the rear surface 101b of the wedge locking ramps 101, 101 and the upper tie wings 105, 105.

Furthermore, the lower tie wings 106, 106 include protuberances 150, 150 extending inward from the left and right sides toward the longitudinal axis L of the slide path SP. When the orthodontic professional is manipulating the clip 3, 13, and 103 downward or from the closed state to the open or unlocked state in the manner described above, the tabs 107a, 107a of the arms 107, 107 contact the protuberances 150, 150, respectively, and are resiliently deflected toward each other or inwardly toward the longitudinal axis L of the slide path SP. Once the tabs 107a, 107a move past or over the protuberances 150, 150, the arms 107, 107 resilient deflect away from each other or away from the longitudinal axis L of the slide path SP and resume their original shape, thereby locking the clip 3, 13, 103 in the coplanar locking recess 140.

Accordingly, regardless of which embodiment of the bracket 110 illustrated in FIGS. 13-18 is being used, an orthodontic professional would position and retain an archwire AW within the archwire slot 102 of the bracket 110 as follows. The clip 103 is manipulated along the slide path SP from the open or unlocked state toward a closed or unlocked state. The front surface 101a of the wedge locking ramp 101 deflects the corresponding tab 107a vertically upward and away from, at an oblique angle relative to the upper surface of the slide path SP, and over the wedge locking ramp 101.

Once the tabs 107a, 107a have passed over and beyond their corresponding wedge locking ramp 101, 101, each tab 107a returns down onto the slide path SP and rests within a recess defined between the rear surface 101b of each ramp 101 and a corresponding upper tie wing 105, wherein each tab 107a is retained or securely locked behind the wedge locking ramp 101 free of any transverse, coplanar or parallel locking force that is exerted by the clip 103. That is, the rear surface 101b of each wedge locking ramp 101 engages and prevents a corresponding tab 107a from sliding toward the open state or lower tie wings 106.

Figure 19:
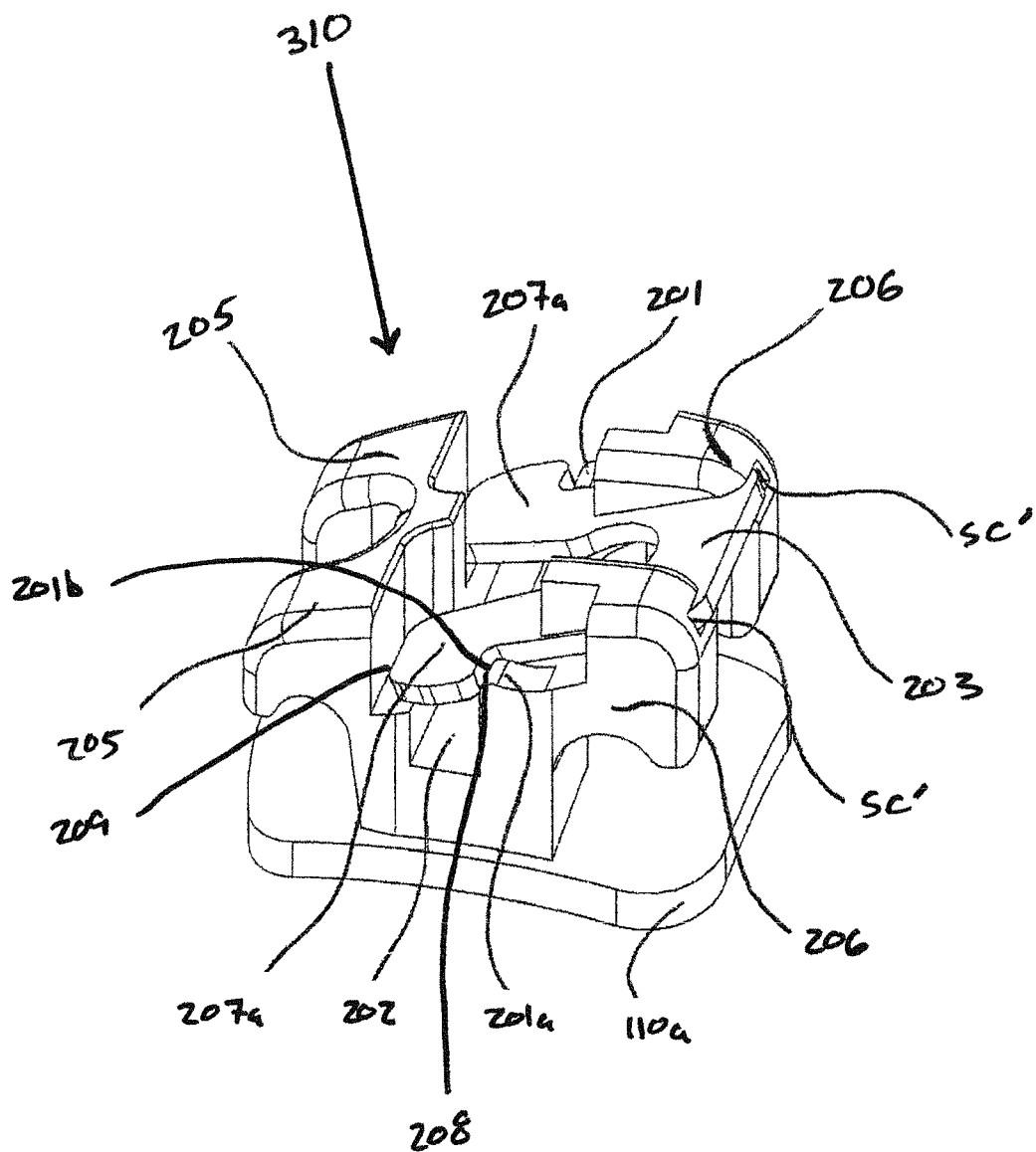
FIG. 19 is a perspective view of a self ligating orthodontic bracket according to a fourth embodiment of the present invention, wherein the bracket and a sliding clip are in the closed or locked state.
Figure 20:
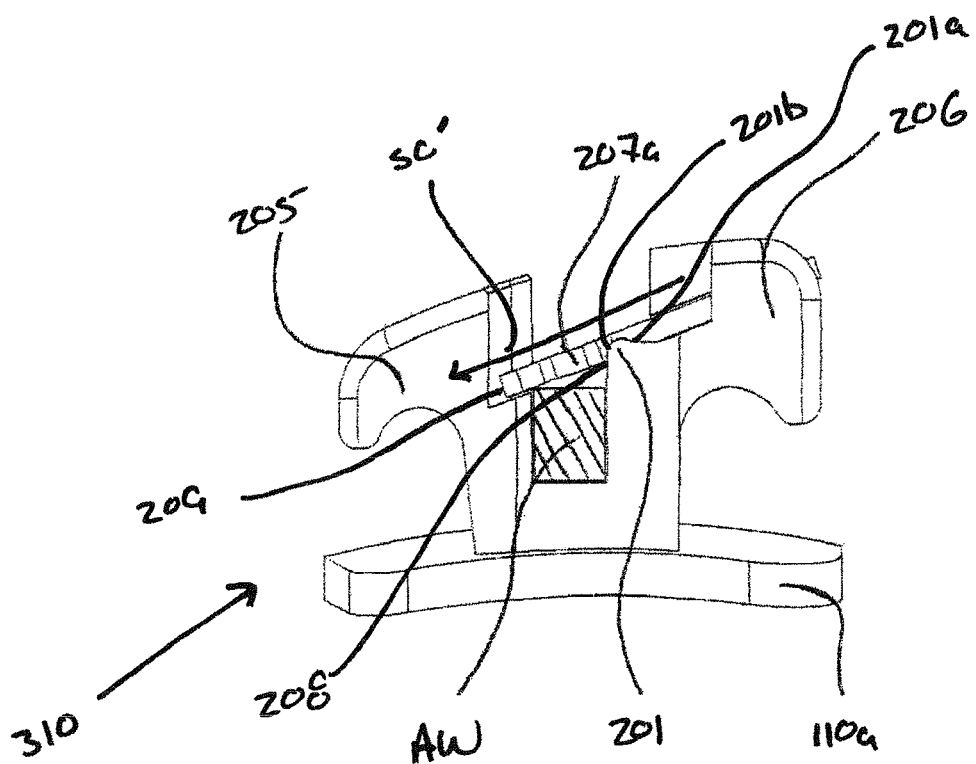
FIG. 20 is a cross-sectional view of the self ligating orthodontic bracket illustrated in FIG. 19.

FIGS. 19 and 20 illustrate a fourth embodiment of the bracket 310 of the present invention, wherein the clip 203 slides along an inclined slide path SP within an inclined slide channel SC' defined by distal and mesial walls of the lower tie wings 206 and oriented transversely relative to the archwire slot 202. Moreover, a wedge locking ramp 201 is provided on the lower tie wing side of the archwire slot 202, wherein a wedge locking ramp 201 is provided on the left and right sides of the slide path SP. It is within the scope of the present invention for the wedge locking ramps 201 to be located preferably adjacent the archwire slot 202 or proximate thereto. Each wedge locking ramps 201 has a sloped or ramped front surface 201a. The clip 203 includes a pair of arms 207, each arm 207 having a tab 207a located at the free end thereof and extending away from the tab 207a of the other arm 207. As shown in FIGS. 19 and 20, each tab 207a is configured to span the entire archwire slot 202 such that when the clip 203 is in the closed or locked state, a first edge 208 engages a rear surface 201b of the corresponding wedge locking ramp 201 and the archwire AW is retained in the archwire slot 202.

Optionally, each tab 207a may also be configured to have a second edge 209 which engages the corresponding upper tie wing 205.

Accordingly, when the clip 203 is slid within the inclined slide channel SC' and along the inclined slide path SP from an open position toward a closed or locked position, the sloped or ramped front surface 201a of the wedge locking ramp 201 deflects the first edge 208 of the corresponding tab 207a vertically upward and away from, at an oblique angle relative to, the slide path SP', over the wedge locking ramp 201, and across the archwire slot 202. Once the tabs 207a, 207a are slid beyond the corresponding wedge locking ramp 201, a portion of each tabs 207a rest on a part of the slide path SP' located on the upper tie wing side of the bracket 210, and a remaining portion of each tab 207a spans an opening of the archwire slot 202. The rear surface 201b of the wedge locking ramp 201 is abutted by the first edge 208 of each tab 207a wherein the tabs 207a, 207a are locked behind the corresponding wedge locking ramp 201 free of a transverse, coplanar or parallel locking force being exerted by the clip 203. The rear surface 201b of each wedge locking ramp 201 prevents the corresponding tab 207a from sliding toward the open position or the lower tie wings 206.

Figure 21:
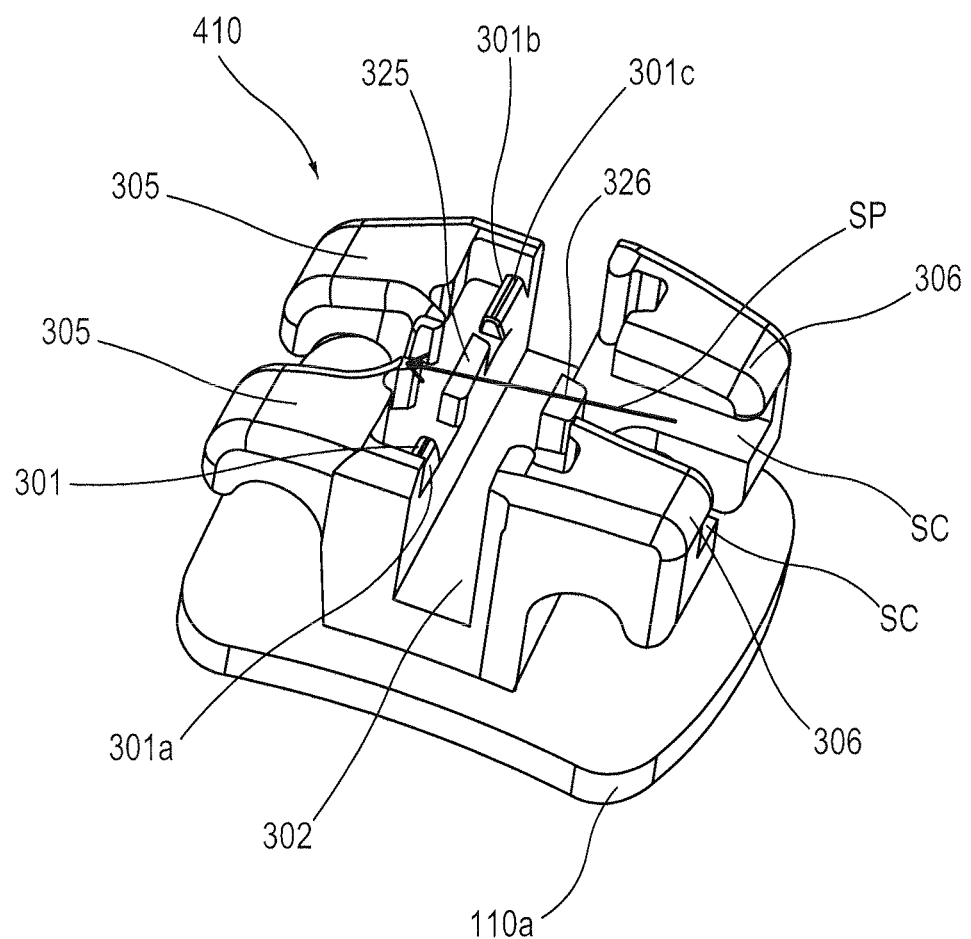
FIG. 21 is a perspective view of a self ligating orthodontic bracket according to a fifth embodiment of the present invention.
Figure 22:
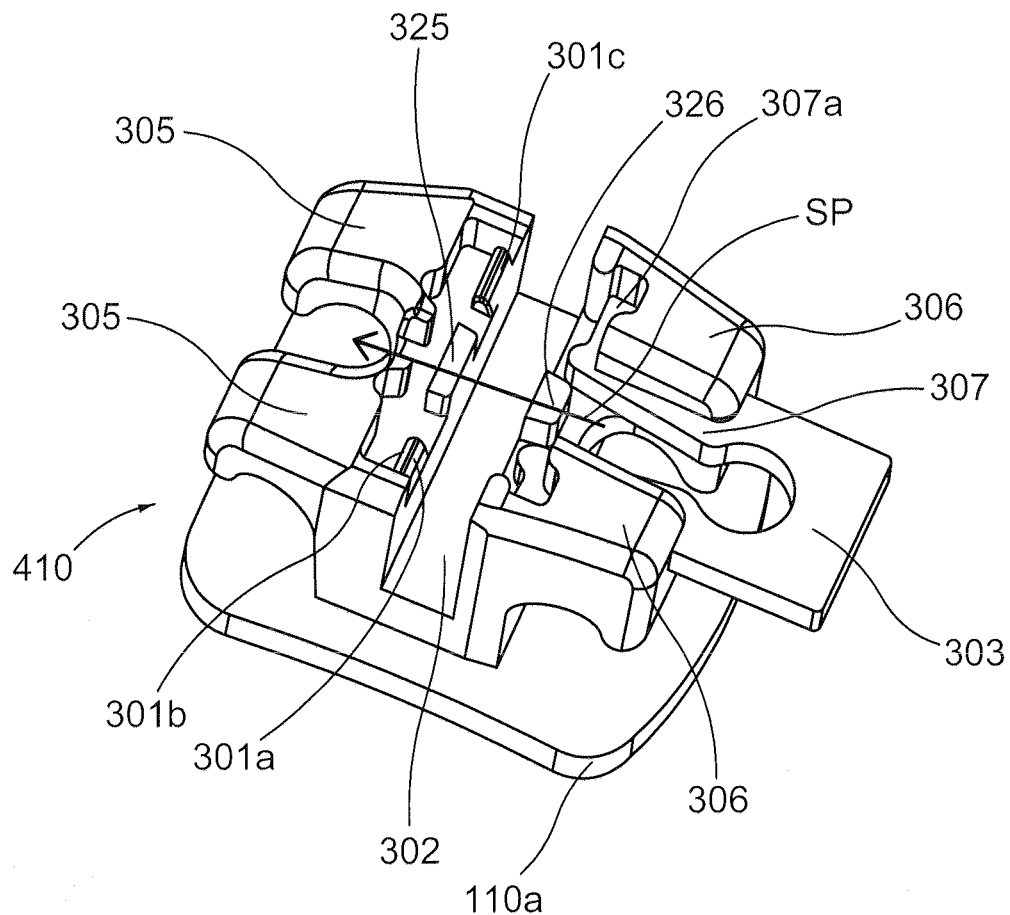
FIG. 22 is a perspective view of the self ligating orthodontic bracket illustrated in FIG. 21, wherein the bracket and a sliding clip are in the open or unlocked state.
Figure 23:
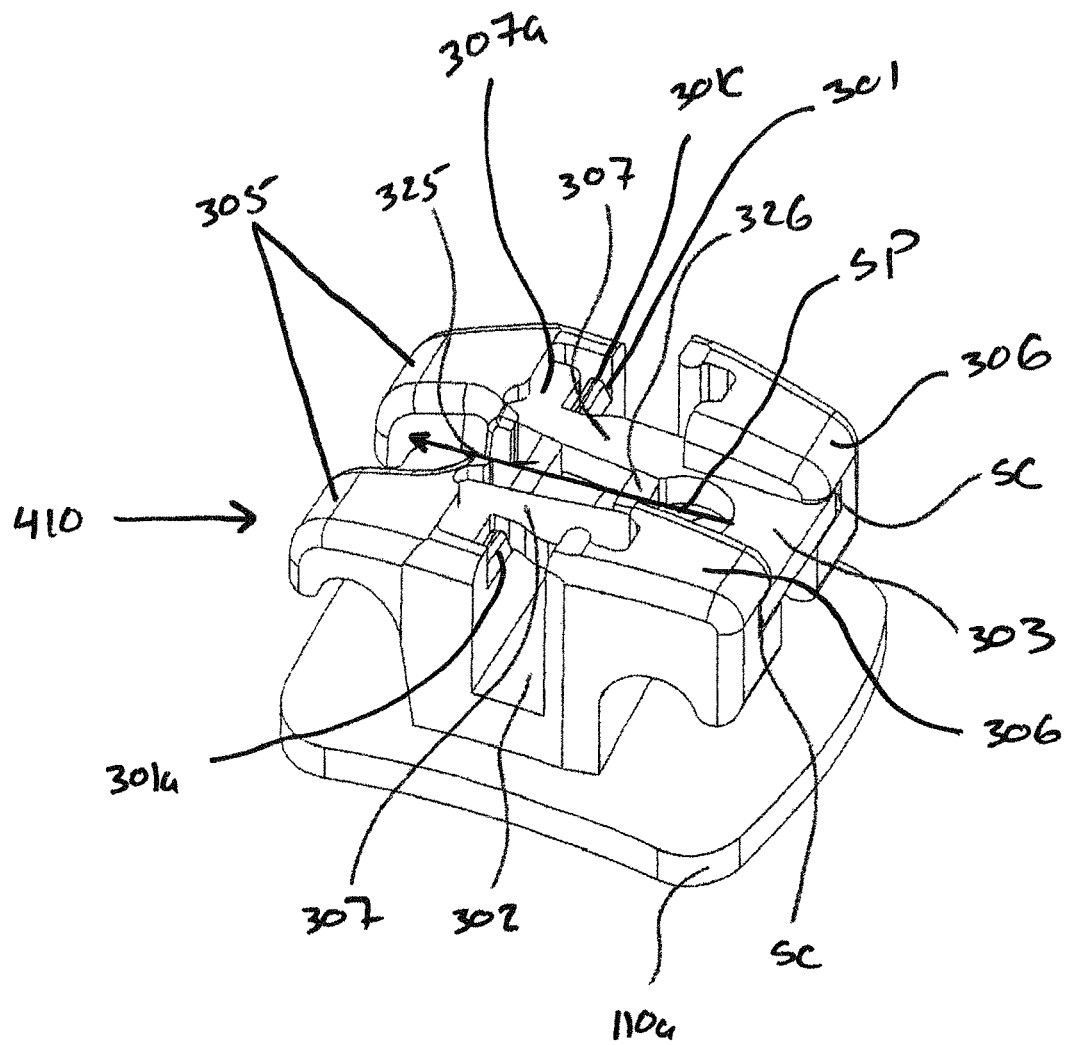
FIG. 23 is a perspective view of the self ligating orthodontic bracket illustrated in FIG. 21, wherein the bracket and a sliding clip are in the closed or locked state.

FIGS. 21-23 illustrate a fifth embodiment of the self ligating orthodontic bracket 410 wherein, as in the above-described third embodiment, a wedge locking ramp 301 is positioned on the left and right sides of the slide path SP. Each wedge locking ramp 301 has a first or front surface 301a facing toward the lower tie wings 306, 306 and extends up and away from an upper surface of the slide path SP. A second or rear surface 301b of each wedge locking ramp 301 faces toward the upper tie wings 305 and extends essentially orthogonally relative to the upper surface of the slide path SP. The front and rear surfaces 301a and 301b of each wedge locking ramp 301 are connected to each other by a transition region 301c. The wedge locking ramps 301, 301 are located on the upper tie wing side of the archwire slot 302 defined in the bracket 410. Moreover, the front surface 301a of each wedge locking ramp 301 may be perpendicular or orthogonal relative to the slide path SP; inclined relative to the slide path SP; or have the wedge locking ramps 301, 301 connected to each other by a beveled wall 170 (FIG. 16) defined along a portion of the upper surface of the slide path SP between the wedge locking ramps 301, 301, wherein the beveled wall 170 facilitates the upward deflection of tabs 307a, 307a extending from corresponding arms 307, 307 of the clip 303.

Moreover, in the fifth embodiment, an upper guiding protuberance 325 and a lower guiding protuberance 326 are provided, respectively, on the upper and lower tie wing sides of the archwire slot 302 and centrally located along the slide path SP. The protuberances 325 and 326 deflect the arms 307, 307 of the clip 303 upward or vertically at an oblique angle relative to the slide path SP or channel SC. When the clip 303 is slid along the slide path SP from the open position toward a closed or locked position, the tabs 307a, 307a are first deflected vertically by the lower guiding protuberance 326, then traverse the archwire slot 302, and are again deflected again vertically by the upper guiding protuberance 325. Once the tabs 307a, 307a are deflected over the upper guiding protuberance 325, the tabs 307a, 307a return down onto the slide path SP wherein the tabs 307a, 307a are locked behind the wedge locking ramps 301, 301 free of a transverse, coplanar or parallel locking force being exerted by the clip 303. The rear surface 301b of each wedge locking ramp 301 prevents the corresponding tab 307a from sliding toward the open position or the lower tie wings 306.

Figure 24:
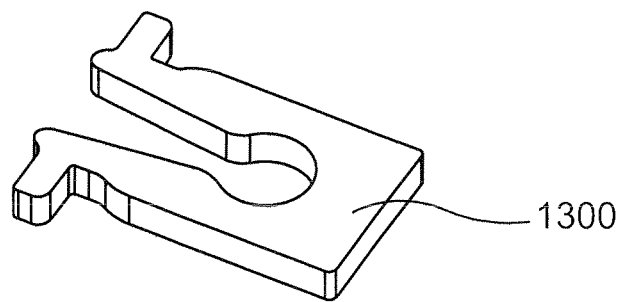
FIG. 24 is a perspective view of a sliding clip.

FIG. 24 is a perspective view of an exemplary embodiment of a sliding clip 1300 manufactured from a material having shape memory.

Preferably, the clip 1300 is manufactured from a shape memory alloy (SMA), which is a metallic alloy capable of returning to a previously defined shape and/or size when subjected to an appropriate thermal procedure. In general, SMAs plastically deform at a relatively low temperature and when exposed to a higher temperature, SMAs return to their previous shape, that is, the shape before exposed to the relatively low temperature. SMAs exhibiting shape memory only upon being heated are commonly referred to as one-way shape memory, while materials which additionally undergo a change in shape during cooling are referred to as two-way shape memory. SMAs have two stable phases, a first phase occurs during the high temperature phase and is referred to as austenite, while a second phase occurs during the low temperature phase and is referred to as martensite. Moreover, the martensite can be one of two forms, twinned and detwinned. A phase transformation which takes place between the austenite and martensite phases upon heating/cooling is known as the basis for the unique aspects provided by SMAs.

For example, if the clip 1300 is manufactured from an SMA material and cooled, in the absence of an applied load, the SMA material transforms from the austenite phase to the martensite phase. Accordingly, the SMA material can transform from the austenite phase wherein the clip 1300 has a previously determined geometric configuration to the martensite phase wherein the clip 1300 transforms, e.g., shrinks, to another configuration.

As applied to the present invention, it is within the scope of the invention wherein the clip 1300 is cooled or transformed from the austenite phase to the martensite phase such that the clip 1300 transforms or shrinks in size and/or configuration. The orthodontic professional then takes the clip 1300 in the martensite phase or shrunken state and inserts the clip 1300 into any of the above-mentioned brackets. Once the clip 1300 is inserted into the bracket that is previously affixed to the surface of a patient's tooth, the temperature of the interior of the patient's mouth will heat the clip 1300, thereby providing the clip 1300 with a reverse transformation from the martensite phase to the austenite phase. That is, the clip 1300 expands or transforms to the previously determined geometric configuration or shape. Accordingly, and by way of example only, the legs, and/or tabs and/or inwardly extending locking tabs of any of the above-described clips would expand or increase in dimensional size, thereby being more securely retained or engaged with the various structural components of the aforementioned brackets, such as, but not limited to, the walls of the lower tie wings which define the slide channel SC, the rear surface of any of the wedge locking ramps, and/or the upper tie wings.

The material and the heat treating processes used to fabricate the shape memory clip 1300 brings versatility in the design and multiple choices in flexibility, geometric configurations, thickness, shape memory recover and martensitic to austenitic transformation from room to mouth temperature.

The shape memory sliding clip 1300 can be formed from any material of sufficient bendability to permit repeated movements or deflections in the assembly, opening and closing operations. More specifically, the material forming the shape memory sliding clip 1300 should undergo elastic deformation without significant plastic deformation when deflected or bent throughout the course of the orthodontic treatment.

Although numerous alloys are known to exhibit shape memory effect, alloys that recover a substantial amount of shape that generates a significant force upon changing shape are considered to be viable for use with the clip 1300 of the inventive bracket described above. Examples of such alloys include, but are in no way limited to, nickel-titanium alloys (e.g., NiTi) and copper-based alloys (e.g., CuZnAl, CuAlNi). It is known that nickel-titanium alloys have greater shape memory strain relative to the copper-based alloys, as well as being more thermally stable, have excellent corrosion resistance and higher ductility. However, it is also known that copper-based alloys cost less than nickel-titanium alloys, are able to be easily melted and extruded in air, and have wider ranges of potential transformation temperatures. The clip 1300 could therefore be manufactured from one of the two alloys described above while taking the advantages and disadvantages noted above into consideration in consideration of the particular application.

Many modifications may be made to adapt the teachings of the bracket of this invention to particular situations or materials without departing from the scope thereof. Therefore, this invention should not be limited to the particular embodiments disclosed herein, but includes all embodiments within the spirit and scope of the disclosure.

For example, the orthodontic bracket illustrated in the attached figures may include such additional features as a low profile due to the design geometry where it is not necessary to have a high profile labial/lingual dimension in order to accommodate the opening and closing mechanism of the bracket and the sliding clip.

Also, the bracket may include rounded edges, a chamfered archwire slot, and a convex shape oriented gingival/occlusal or gingival/incisal to help avoid lip interference, thereby improving patient comfort and adaptation to the appliance.

Further, the upper and lower tie wings may be configured to provide sufficiently ample space under the tie wings to facilitate attaching or ligating accessories and auxiliaries different from other self ligating brackets that lack such an important feature.

What is claimed is:
1. A self ligating orthodontic bracket system comprising:
   a bracket comprising:
      an archwire slot defined therein, the archwire slot configured to receive an archwire therein,
      a slide channel defining a slide path and configured to slidably receive a planar ligating member therein, wherein an upwardly facing surface defines a lower boundary of the slide channel; and
      at least one wedge locking ramp disposed on the upwardly facing surface and along the slide path, wherein a surface of the at least one wedge locking ramp is continuous with an upwardly extending wall of the archwire slot;
   a planar ligating member slidable along the slide path, the slide path extends transverse relative to the archwire slot and through the slide channel;
   wherein the at least one wedge locking ramp is configured to deflect the planar ligating member vertically upward and away from the upwardly facing surface and over the at least one wedge locking ramp when the ligating member travels along the slide path from an unlocked position to a locked position.

2. The system according to claim 1, wherein the archwire slot is configured to securely retain an archwire in the archwire slot when the ligating member is in the locked position.

3. The system according to claim 1, wherein the at least one wedge locking ramp comprises a front surface facing a first end of the bracket, the front surface extending up and away from the upwardly facing surface.

4. The system according to claim 3, wherein the front surface of the at least one wedge locking ramp extends up and away from the upwardly facing surface in an oblique manner.

5. The system according to claim 3, wherein the surface of the at least one wedge locking ramp which is continuous with an upwardly extending wall of the archwire slot is a rear surface facing a second end of the bracket opposite the first end of the bracket and extends orthogonally relative to the upwardly facing surface.

6. The system according to claim 5, wherein the front surface of the at least one wedge locking ramp and the rear surface of the at least one wedge locking ramp are joined to each other by a transition region provided therebetween.

7. The system according to claim 6, wherein the transition region is arcuate.

8. The system according to claim 5, wherein the bracket further comprises:
  a pair of lower ties wings located at the first end of the bracket; and
  a pair of upper ties wings located at the second end of the bracket.

9. The system according to claim 1, wherein the planar ligating member comprises:
  a body portion; and
  a pair of arms extending away from the body portion in a direction extending from the first end of the bracket toward the second end of the bracket.

10. The system according to claim 9, wherein each arm includes a tab extending parallel to the archwire slot from a free end of the corresponding arm.

11. The system according to claim 10, wherein the tab of each arm extends either toward the other tab or away from the other tab.

12. The system according to claim 1, wherein the archwire slot is disposed intermediate opposing first and second ends of the bracket, and the at least one wedge locking ramp overlaps a longitudinal axis of the slide path, the longitudinal axis extending from the first end of the bracket to the second end of the bracket.

13. The system according to claim 1, wherein the at least one wedge locking ramp comprises a first wedge locking ramp and a second wedge locking ramp, and wherein the first and second wedge locking ramps are spaced from a longitudinal axis of the slide path by a predetermined distance.

14. The system according to claim 13, wherein the first and second wedge locking ramps are connected to each other by a beveled wall.

15. The system according to claim 13, wherein the bracket further comprises a pair of lower tie wings located at a first end of the bracket, at least one of the lower tie wings includes a protuberance extending inward toward a longitudinal axis of the slide path.

16. The system according to claim 15, wherein the protuberance is located adjacent the archwire slot.

17. The system according to claim 16, wherein a coplanar locking recess is defined between the protuberance and a free end of the at least one lower tie wing.

18. The system according to claim 13, wherein a first guiding protuberance is disposed between the first and second wedge locking ramps.

19. The system according to claim 18, further comprising a second guiding protuberance, wherein the second guiding protuberance is located on an opposite side of the archwire slot than the first guiding protuberance.

20. The system according to claim 19, wherein the first and second guiding protuberances each overlap the longitudinal axis of the slide path.

21. The system according to claim 1, wherein the archwire slot is defined by a first upstanding wall opposite a second upstanding wall, the second upstanding wall being shorter than the first upstanding wall, and wherein the planar ligating member travels downward in a direction extending from the first upstanding wall toward the second upstanding wall when the planar ligating member travels from the unlocked position to the locked position.

22. The system according to claim 21, wherein the at least one locking ramp is provided between the archwire slot and a first end of the bracket.

23. The system according to claim 22, wherein the planar ligating member comprises:
  a body portion; and
  a pair of arms extending away from the body portion in a direction extending from the first end of the bracket toward a second end of the bracket opposite the first end.

24. The system according to claim 23, wherein each arm includes a tab extending parallel to the archwire slot from a free end of the corresponding arm.

25. The system according to claim 24, wherein the tab of each arm extends either toward the other tab or away from the other tab.

26. The system according to claim 24, wherein each tab includes a first surface and a second surface facing away from the first surface, the planar second surface of each tab contacting the at least one wedge locking ramp when the planar ligating member is in the locked position.

27. The system according to claim 26, wherein the first surface of each tab contacts a surface of a tie wing located on the second end of the bracket.

28. The system according to claim 1, wherein the planar ligating member is manufactured from a shape memory material.

29. The system according to claim 28, wherein the shape memory material is an alloy.

30. The system according to claim 29, wherein the alloy is a metallic alloy which plastically deforms at a first temperature and transforms back to an original configuration at a second temperature.

31. The system according to claim 30, wherein the first temperature is less than the second temperature.

32. The system according to claim 30, wherein the metallic alloy is selected from one of NiTi, CuZnAl, and CuAlNi.

* * * * *